US008039620B2

(12) United States Patent
Ahmad et al.

(10) Patent No.: US 8,039,620 B2
(45) Date of Patent: Oct. 18, 2011

(54) VARENICLINE TOSYLATE, AN INTERMEDIATE IN THE PREPARATION PROCESS OF VARENICLINE L-TARTRATE

(75) Inventors: Suhail Ahmad, New Delhi (IN); Vinod Kumar Kansal, Haryana (IN); Maytal Piran, Rishon LeZion (IL); Zvi Harel, Kfar Saba (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 65 days.

(21) Appl. No.: 12/470,137

(22) Filed: May 21, 2009

(65) Prior Publication Data

US 2010/0004451 A1 Jan. 7, 2010

Related U.S. Application Data

(60) Provisional application No. 61/153,390, filed on Feb. 18, 2009, provisional application No. 61/190,284, filed on Aug. 26, 2008, provisional application No. 61/135,359, filed on Jul. 17, 2008, provisional application No. 61/128,649, filed on May 22, 2008.

(51) Int. Cl.
*C07D 497/00* (2006.01)
(52) U.S. Cl. ........................ 544/345; 540/586
(58) Field of Classification Search .............. 544/345; 540/586
See application file for complete search history.

(56) References Cited

U.S. PATENT DOCUMENTS

| | | |
|---|---|---|
| 6,410,550 B1 | 6/2002 | Coe et al. |
| 6,558,435 B2 | 5/2003 | Am Ende et al. |
| 6,605,610 B1 | 8/2003 | Coe et al. |
| 6,787,549 B2 | 9/2004 | Johnson et al. |
| 6,794,388 B2 | 9/2004 | Quallich et al. |
| 6,887,884 B2 | 5/2005 | Coe et al. |
| 6,890,927 B2 | 5/2005 | Bogle et al. |
| 6,897,310 B2 | 5/2005 | Coe et al. |
| 6,951,938 B2 | 10/2005 | Coe et al. |
| 7,009,073 B2 | 3/2006 | Watson et al. |
| 7,091,372 B2 | 8/2006 | Singer et al. |
| 7,144,882 B2 | 12/2006 | Coe et al. |
| 7,186,870 B2 | 3/2007 | Singer et al. |
| 7,205,300 B2 | 4/2007 | Coe et al. |
| 7,265,119 B2 | 9/2007 | Bogle et al. |
| 2002/0072524 A1 | 6/2002 | Wadsworth et al. |
| 2003/0060624 A1 | 3/2003 | Singer |
| 2003/0134844 A1 | 7/2003 | Saltarelli |
| 2003/0166701 A1 | 9/2003 | Bogle et al. |
| 2003/0180360 A1 | 9/2003 | Am Ende et al. |
| 2004/0082555 A1 | 4/2004 | Villalobos |
| 2004/0235850 A1 | 11/2004 | Waterman |
| 2005/0004379 A1 | 1/2005 | Handfield, Jr. et al. |
| 2005/0250806 A1 | 11/2005 | Saltarelli |
| 2006/0057207 A1 | 3/2006 | Ziegler et al. |
| 2006/0084656 A1 | 4/2006 | Ziegler et al. |
| 2007/0066827 A1 | 3/2007 | Handfield, Jr. et al. |
| 2007/0185327 A1 | 8/2007 | Rainville et al. |
| 2007/0224690 A1 | 9/2007 | Busch et al. |
| 2007/0248671 A1 | 10/2007 | Johnson et al. |
| 2007/0275973 A1 | 11/2007 | Coe et al. |
| 2008/0026059 A1 | 1/2008 | Waterman |

FOREIGN PATENT DOCUMENTS

| | | |
|---|---|---|
| EP | 1157726 | 11/2001 |
| EP | 1 659 114 | 5/2006 |
| WO | WO 99/35131 | 7/1999 |
| WO | WO 01/62736 | 8/2001 |
| WO | WO 01/85688 | 11/2001 |
| WO | WO 02/085843 | 10/2002 |
| WO | WO 02/092089 | 11/2002 |
| WO | WO 02/092597 | 11/2002 |
| WO | WO 03/045394 | 6/2003 |
| WO | WO 03/045437 | 6/2003 |
| WO | WO 2004/046077 | 6/2004 |
| WO | WO 2004/048318 | 6/2004 |
| WO | WO 2004/063164 | 7/2004 |
| WO | WO 2004/108725 | 12/2004 |
| WO | WO 2006/090236 | 8/2006 |
| WO | WO 2006/100595 | 9/2006 |
| WO | WO 2006/117672 | 11/2006 |
| WO | WO 2007/012963 | 2/2007 |
| WO | WO 2007/110730 | 10/2007 |
| WO | WO 2008/060487 | 5/2008 |
| WO | WO 2009/065872 | 5/2009 |
| WO | WO 2009/109651 | 9/2009 |
| WO | WO 2010/023561 | 3/2010 |
| WO | WO 2010/151524 | 12/2010 |

OTHER PUBLICATIONS

Perry's Chemical Engineer's Handbook, 6th ed., pp. 20-54 to 20-57, 1984.
Remington: The Science and Practice of Pharmacy, 19th ed., vol. 2, pp. 1627-1628. (1995).
"Loss on Drying", "Physical Test and Determination", LPS 29-NF24, Aug. 1, 2006, Physical Test and Determination, The United States Pharmacopeial Convention. International Search Report and Written Opinion, dated Mar. 23, 2010, from corresponding International Patent Application PCT/US2009/044844.

*Primary Examiner* — James O Wilson
*Assistant Examiner* — Douglas M Willis
(74) *Attorney, Agent, or Firm* — Kenyon & Kenyon LLP

(57) ABSTRACT

Crystalline forms of Varenicline Tosylate:

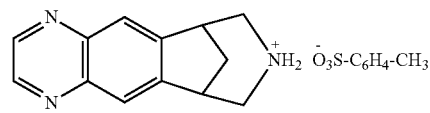

are provided, along with processes for preparing those crystalline forms of Varenicline Tosylate, and processes for obtaining high purity Varenicline base using Varenicline Tosylate.

11 Claims, 13 Drawing Sheets

VARENICLINE TOSYLATE, AN INTERMEDIATE IN THE PREPARATION PROCESS OF VARENICLINE L-TARTRATE

RELATED APPLICATIONS

This application claims benefit of U.S. Provisional Patent Applications Nos. 61/153,390, filed Feb. 18, 2009, 61/190,284, filed Aug. 26, 2008, 61/135,359, filed Jul. 17, 2008, and 61/128,649, filed May 22, 2008, the contents of which are incorporated herein in their entirety by reference.

FIELD OF THE INVENTION

The present invention is directed to crystal forms of Varenicline Tosylate, methods for the preparation of the crystal forms, and processes for preparing high purity Varenicline base from Varenicline Tosylate.

BACKGROUND OF THE INVENTION

Varenicline tartrate salt, 7,8,9,10-tetrahydro-6,10-methano-6H-pyrazino[2,3-h][3]benzazepine, (2R,3R)-2,3-dihydroxybutanedioate (1:1), has a molecular weight of 361.35 Daltons and is described according to the following formula:

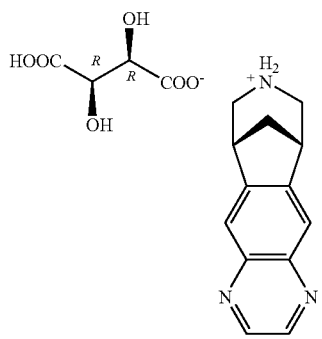

Varenicline tartrate is marketed by Pfizer under the trade name of CHANTIX™ as a partial agonist selective for certain subtypes of nicotinic receptors and indicated for smoking cessation.

Varenicline base and a variety of salts thereof are disclosed in U.S. Pat. No. 6,410,550, EP 1044189, and EP 1659114.

Crystalline forms of Varenicline citrate and succinate salts are described in the U.S. Pat. Nos. 6,787,549 and 6,794,388, respectively.

Varenicline L-tartrate and its crystalline forms A, B, and C are described in the U.S. Pat. Nos. 6,890,927 and 7,265,119.

SUMMARY OF THE INVENTION

The present invention provides crystal forms of Varenicline Tosylate, 5,8,14-Triazatetracyclo[10.3.1.0$^{2,11}$.0$^{4,9}$]hexa-deca-2(11),3,5,7,9-pentaene tosylate, having the following formula:

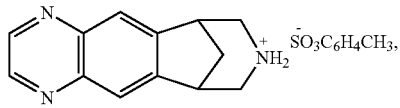

methods of preparing the crystal forms of Varenicline Tosylate of the invention, and processes for preparing high purity Varenicline base from Varenicline Tosylate.

Varenicline Tosylate is preferably isolated as a solid, more preferably as solid and even more preferably as a crystal form.

Varenicline Tosylate described above can be characterized by data selected from $^1$HNMR spectrum (400 MHz, DMSO-d$_6$) having peaks at about δ. 8.931-8.050 (4H), 7.47-7.12 (4H), 3.6 (br s 2H), 3.49-3.18 (4H), and 2.293-2.191 (5H), a $^{13}$CNMR spectrum (100.61 MHz, DMSO-d$_6$) having peaks at about δ. 150.97, 148.20, 143.12, 133.36, 130.68, 129.32, 53.83, 51.96, 45.28, 45.08, 43.26, and 26.00, an $^1$HNMR spectrum as depicted in FIG. 1, a $^{13}$CNMR spectrum as depicted in FIG. 2, and combinations thereof.

Varenicline Tosylate can be prepared by combining Varenicline base, a solvent and p-Toluene sulfonic acid (p-TSA) to obtain a reaction mixture and precipitating Varenicline Tosylate from the reaction mixture. Preferably, the obtained Varenicline Tosylate is further recovered from the reaction mixture.

Varenicline base, p-TSA and at least one solvent can be combined to form a reaction mixture at about room temperature. Varenicline Tosylate then precipitates out of the mixture.

A reaction mixture of p-TSA, Varenicline base, and a solvent may be heated and further cooled to facilitate precipitation of Varenicline Tosylate.

The present invention provides a crystalline form of Varenicline Tosylate, designated form I, characterized by data selected from a group consisting of a powder XRD pattern having peaks at about 10.1, 13.0, and 18.7±0.2 degrees two theta and at least two peaks selected from the group consisting of 11.5, 14.2, 16.7, 19.3, and 20.6±0.2 degrees two theta, a powder XRD pattern having peaks at about 10.1, 13.0, 16.7, 18.7 and 20.6±0.2 degrees two theta, a powder XRD pattern having peaks at about 10.2, 13.1, 16.8, 19.4, 23.0±0.1 degrees two theta, a powder XRD pattern substantially as depicted in FIGS. 4 and 5, and combinations thereof.

The above crystalline form I may be further characterized by additional peaks selected from a group consisting of a powder XRD pattern having peaks at about 11.5, 14.2, 17.4, 19.3 and 22.3±0.2 degrees two theta, a powder XRD pattern having peaks at about 14.3, 18.5, 18.9, 23.5 and 26.8±0.1 degrees two theta and combinations thereof.

Crystalline form I of Varenicline Tosylate may be prepared by a process comprising; combining Varenicline Base, a C$_1$-C$_6$ alcohol and p-Toluene sulfonic acid to obtain a reaction mixture, heating and then cooling the obtained reaction mixture.

Alternatively, crystalline form I of Varenicline Tosylate may be prepared by a process comprising heating a mixture of Varenicline Base in a C$_1$-C$_6$ alcohol and p-TSA, and further cooling the mixture.

The present invention also provides a crystalline form of Varenicline Tosylate, designated form II, characterized by data selected from a group consisting of a powder XRD pattern having peaks at about 11.6, 12.9, 13.3, 20.8, and 21.3±0.2 degrees two theta, a powder XRD pattern having peaks at about 11.6, 12.9, 13.3, 21.3 and 23.3±0.2 degrees two theta, a powder XRD pattern having peaks at about 5.8, 10.0, 17.4, 19.1, 23.3±0.1 degrees two theta, a powder XRD pattern substantially as depicted in FIGS. 6 and 7 and combinations thereof.

The above crystalline form II may be further characterized by additional peaks selected from a group consisting of a powder XRD pattern having peaks at about 5.8, 10.0, 16.9, 17.4, and 18.8±0.2 degrees two theta, a powder XRD pattern having peaks at about 11.5, 13.2, 20.8, 22.5 and 25.4±0.1 degrees two theta, and combinations thereof.

Crystalline form II of Varenicline Tosylate may be prepared by a process comprising; combining Varenicline Base, methanol, a $C_6$-$C_{12}$ aromatic hydrocarbon, and p-Toluene sulfonic acid to obtain a reaction mixture, heating and cooling the obtained reaction mixture.

Alternatively, crystalline form II of Varenicline Tosylate may be prepared by a process comprising heating a mixture of Varenicline base in methanol, $C_6$-$C_{12}$ aromatic hydrocarbon, and p-TSA, and cooling the mixture.

The present invention also provides a crystalline form of Varenicline Tosylate, designated form III, characterized by a powder XRD pattern having peaks at about 10.0, 11.6, 17.4, 22.3, and 22.8±0.2 degrees two theta and additional peaks at about 5.8, 18.8, 19.3, 20.8, and 23.2±0.2 degrees two theta, as depicted in the PXRD diffraction of FIGS. 8, 9 and/or 10.

In particular, Varenicline Tosylate form III can be characterized by a powder XRD pattern having peaks at about 10.0, 11.6, 17.4, 22.3, and 22.8±0.2 degrees two theta.

The Varenicline Tosylate form III described above can be further characterized by data selected from the group consisting of a powder XRD pattern having peaks at about 5.8, 18.8, 19.3, 20.8, and 23.2±0.2 degrees two theta, a powder XRD pattern having peals at about 5.9, 18.9, 19.3, 20.8 and 26.4±0.2 degrees two theta and combinations thereof.

The present invention also provides a process for preparing Varenicline Tosylate form III, comprising exposing Varenicline Tosylate form II to less than about 5 percent relative humidity, for a period sufficient to convert form II to form III. Preferably, the relative humidity is 0 percent.

The present invention also provides a process for preparing Varenicline Tosylate form III by heating Varenicline Tosylate form II for a period sufficient to convert form II to form II. The heating is preferably to a temperature of about 70° C. to about 100° C., and more preferably to about 80° C.

The present invention also provides a crystalline form of Varenicline Tosylate, designated form IV, characterized by a powder XRD pattern having peaks at about 11.6, 13.2, 19.5, 23.0, and 24.4±0.2 degrees two theta and additional peaks at about 10.3, 16.9, 18.9, 20.7, and 22.5±0.2 degrees two theta as depicted in the PXRD diffraction of FIGS. 11 and 12.

In particular, Varenicline Tosylate form IV can be characterized by a powder XRD pattern having peaks at about 11.6, 13.2, 19.5, 23.0, and 24.4±0.2 degrees two theta.

The Varenicline Tosylate form IV described above can be further characterized by a powder XRD pattern having peaks at about 10.3, 16.9, 18.9, 20.7, and 22.5±0.2 degrees two theta.

The present invention provides a process for preparing Varenicline Tosylate form IV, comprising: combining Varenicline base, a $C_1$-$C_6$ alcohol, a $C_1$-$C_3$ halogenated aliphatic hydrocarbon and p-Toluene sulfonic acid (p-TSA) to obtain a reaction mixture, and heating and then cooling the obtained reaction mixture.

The present invention also provides a process for preparing Varenicline Tosylate form IV, comprising wetting Varenicline Tosylate form II with water, and grinding the wetted material. Preferably about 100 mg to about 200 mg Varenicline Tosylate form II is wetted with about 1 to about 2 drops of water.

The present invention also provides a process for preparing Varenicline Tosylate form IV, comprising exposing Varenicline Tosylate form II to a relative humidity of from about 80 percent to about 100 percent for a period sufficient to convert form II to form IV. Preferably, the exposure is for a period of about 1 to about 15 days. More, preferably, for about 1 day.

The present invention encompasses pure Varenicline Tosylate. Preferably, the Varenicline Tosylate of the present invention has a total purity of greater than 97 percent by area HPLC, more preferably greater than 99 percent, and even more preferably 99.99 percent by area HPLC.

The present invention further encompasses pure Varenicline base. Preferably, the Varenicline base of the present invention has a total purity of greater than 97 percent by area HPLC, more preferably greater than 99 percent, and even more preferably the purity if 99.97 percent by area HPLC.

The present invention also provides a process for obtaining pure Varenicline base, comprising slurrying Varenicline Tosylate in water with a base and an inert organic solvent. Preferably, the water used is demineralized water (DM water).

Varenicline base obtained according to the process described above is preferably obtained with a total purity of greater than 97 percent by area HPLC, more preferably with a purity of 99.97 percent by area HPLC.

Optionally, the pure Varenicline base obtained according to the process described above is precipitated from the reaction mixture with an organic solvent.

The present invention also provides a process for preparing Varenicline L-Tartrate, comprising obtaining a Varenicline Tosylate according to any of the processes described above, and converting it to Varenicline L-Tartrate.

DETAILED DESCRIPTION OF THE INVENTION

The present invention provides crystal forms of Varenicline Tosylate, 5,8,14-Triazatetracyclo[10.3.1.0$^{2,11}$.0$^{4,9}$]hexadeca-2(11),3,5,7,9-pentaene tosylate, having the following formula:

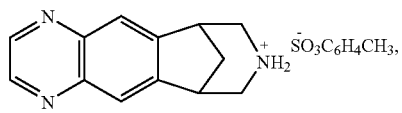

methods of preparing the crystal forms of Varenicline Tosylate of the invention, and processes for preparing high purity Varenicline base from Varenicline Tosylate.

As used herein, "Varenicline base product" refers to the Varenicline base obtained following the conversion of Varenicline Tosylate to Varenicline base.

Varenicline Tosylate is preferably isolated as a solid and more preferably as a crystal form. The use of Varenicline Tosylate as an intermediate salt for preparation of Varenicline base, 5,8,14-Triazatetracyclo[10.3.1.0$^{2,11}$.0$^{4,9}$]hexadeca-2(11),3,5,7,9-pentaene, having the following formula:

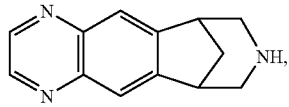

allows obtaining such Varenicline base in a relatively high purity. The purer Varenicline base obtained according to the present invention may be further converted to Varenicline L-tartrate salt.

Figure 1:
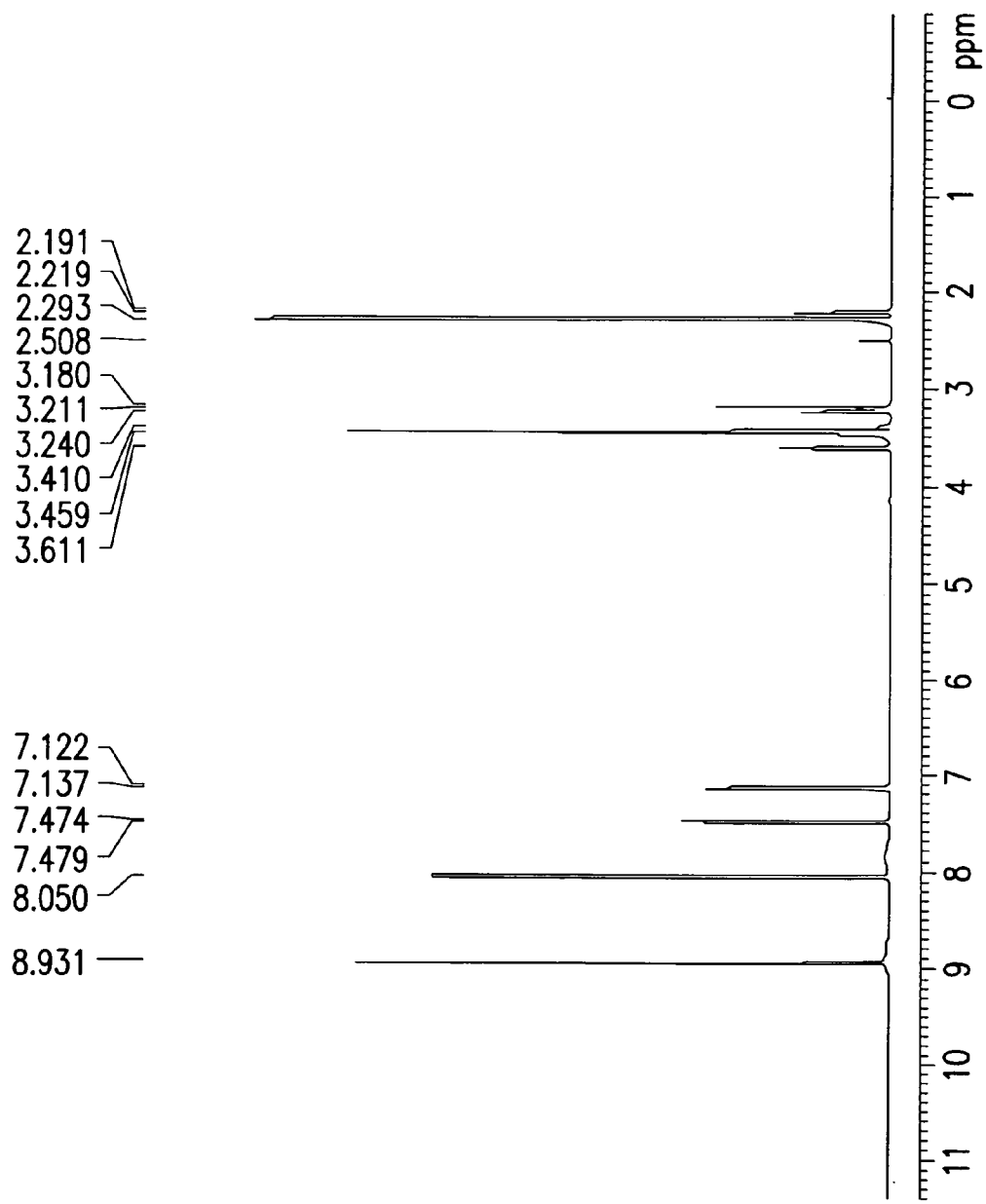
FIG. 1 illustrates $^1$H NMR spectrum of Varenicline Tosylate.
Figure 2:
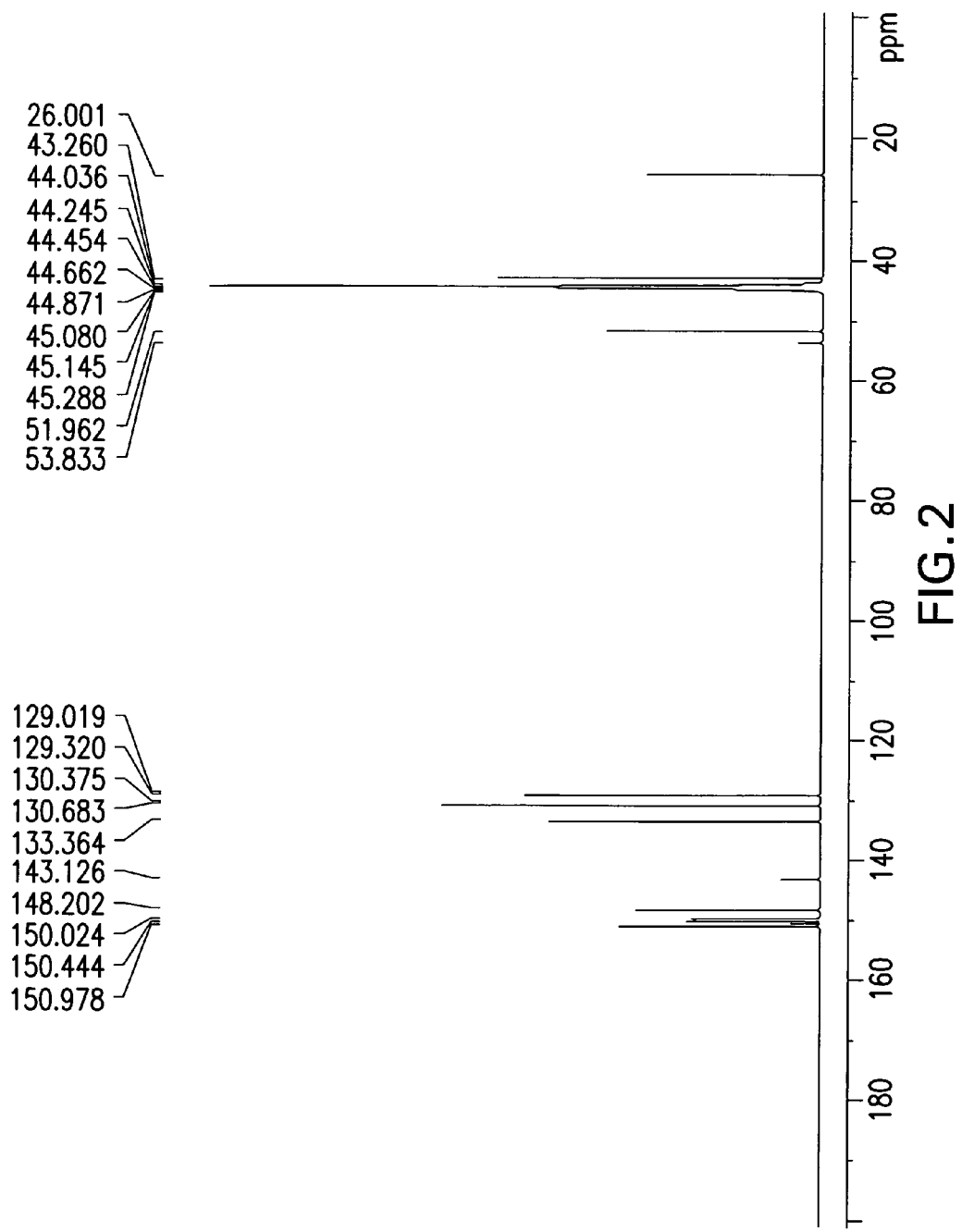
FIG. 2 illustrates $^{13}$C NMR spectrum of Varenicline Tosylate.
Figure 3:
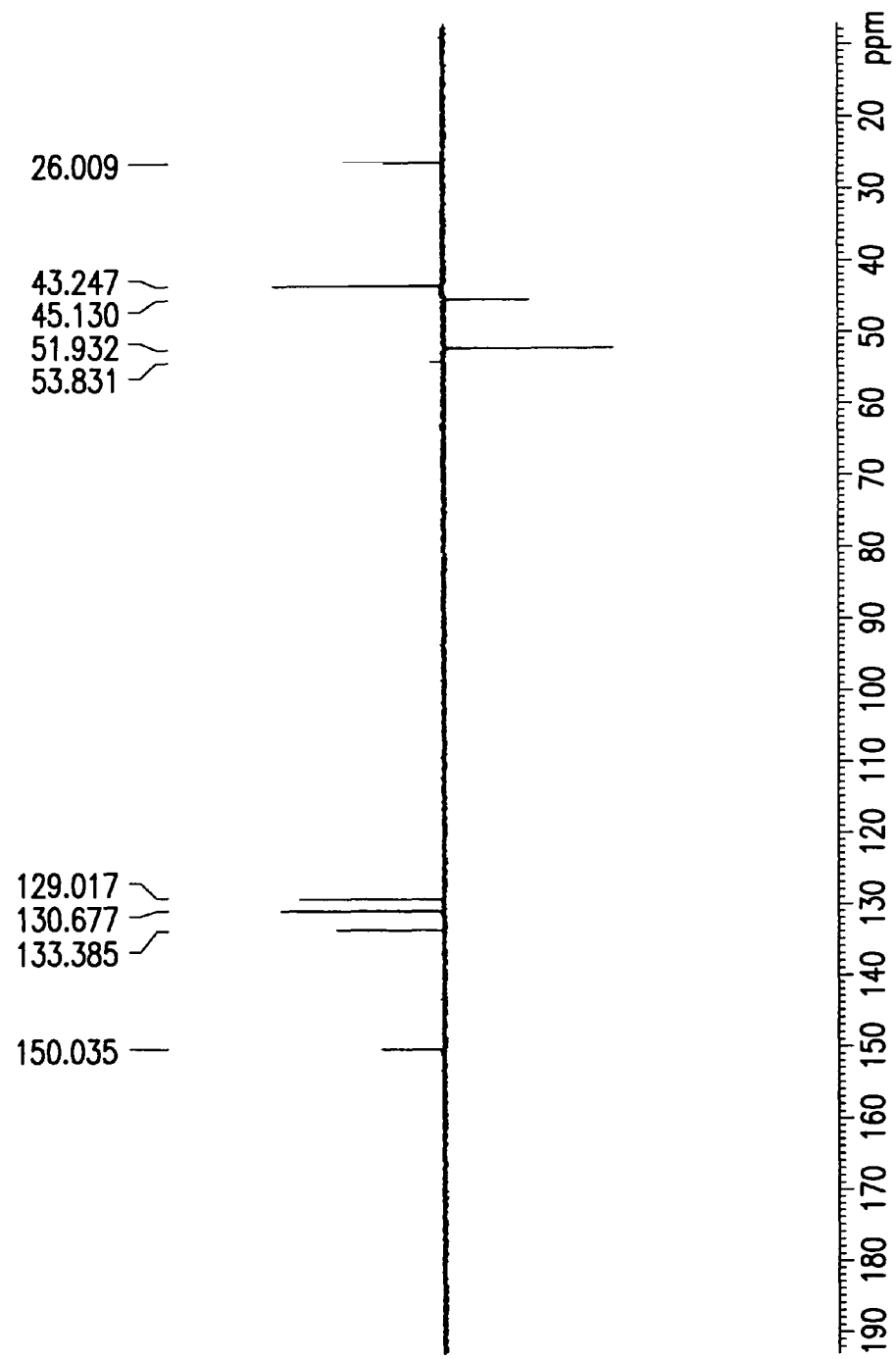
FIG. 3 illustrates $^{13}$C NMR DEPT spectrum of Varenicline Tosylate.

Varenicline Tosylate described above can be characterized by data selected from a $^1$HNMR spectrum (400 MHz, DMSO-d$_6$) having peaks at about δ. 8.931-8.050 (4H), 7.47-7.12 (4H), 3.6 (br s 2H), 3.49-3.18 (4H) and 2.293-2.191 (5H), a $^{13}$CNMR spectrum (100.61 MH$_Z$, DMSO-d$_6$) having peaks at about δ. 150.97, 148.20, 143.12, 133.36, 130.68, 129.32, 53.83, 51.96, 45.28, 45.08, 43.26 and 26.00, a $^1$HNMR spectrum as depicted in FIG. 1, a $^{13}$CNMR spectrum as depicted in FIG. 2, and combinations thereof.

Varenicline Tosylate may be prepared by combining Varenicline base, a solvent, and p-Toluene sulfonic acid (p-TSA) to create a reaction mixture. Varenicline Tosylate forms in such reaction mixture through contact of Varenicline base with p-TSA.

A solution or a suspension of Varenicline base, a solvent and p-TSA may be combined to form a reaction mixture, followed by precipitation and recovery of the Varenicline Tosylate salt from the mixture. The p-TSA may be added either as a solid or as a solution or suspension in a solvent. The organic solvent present in the reaction mixture is preferably selected from the group consisting of C$_{1-8}$ alcohols, C$_{3-7}$ esters, C$_{3-8}$ ethers, C$_{3-7}$ ketones, C$_{6-12}$ aromatic hydrocarbons, acetonitrile, water, and mixtures thereof. Preferably, the solvent is selected from C$_{1-8}$ alcohols and C$_{6-12}$ aromatic hydrocarbons. More preferably, the solvent is selected from isopropyl alcohol (IPA), methanol, toluene, and mixtures thereof.

Varenicline base, p-TSA, and at least one solvent may be combined to form a reaction mixture at about room temperature (in this application the term "room temperature" encompasses a range of preferably about 15° C. to about 25° C.). The amount of p-TSA present in such reaction mixture is preferably to the point of saturation. Varenicline Tosylate then precipitates out of the mixture. Such precipitation may occur on its own or be induced. The reaction mixture may be stirred before, during, or after precipitation.

P-TSA and Varenicline base and at least one solvent may be combined to form a reaction mixture, which is further heated and then cooled to facilitate precipitation of Varenicline Tosylate. Heating may be carried out from about room temperature to about the reflux temperature of the solvent. Cooling is generally to a temperature of about 50° C. or less, preferably about room temperature, to facilitate precipitation. The reaction mixture may be stirred before, during, or after precipitation.

The resulting precipitate from any of the above embodiments may be recovered by various techniques, such as filtration. The precipitate may be dried under ambient or reduced pressure (pressure of less then about one atmosphere), and/or elevated temperature. The precipitate may be dried at room temperature at a pressure of about 400 to about 750 mm Hg and a temperature of about 40° C. to about 70° C.

In accordance with the invention, Varenicline Tosylate can be prepared in different polymorphic forms. Polymorphism, the occurrence of different crystal forms, is a property of some molecules and molecular complexes. A single molecule, such as Varenicline Tosylate may give rise to a variety of crystalline forms having distinct crystal structures and physical properties like melting point, X-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC"), which have been used to distinguish polymorphic forms.

The difference in the physical properties of different crystalline forms results from the orientation and intermolecular interactions of adjacent molecules or complexes in the bulk solid. Accordingly, polymorphs are distinct solids sharing the same molecular formula, yet having distinct physical properties that can be advantageous in certain applications compared to other crystalline forms of the same compound or complex. Therefore, processes for the preparation of polymorphic forms of Varenicline Tosylate are desirable.

Figure 4:
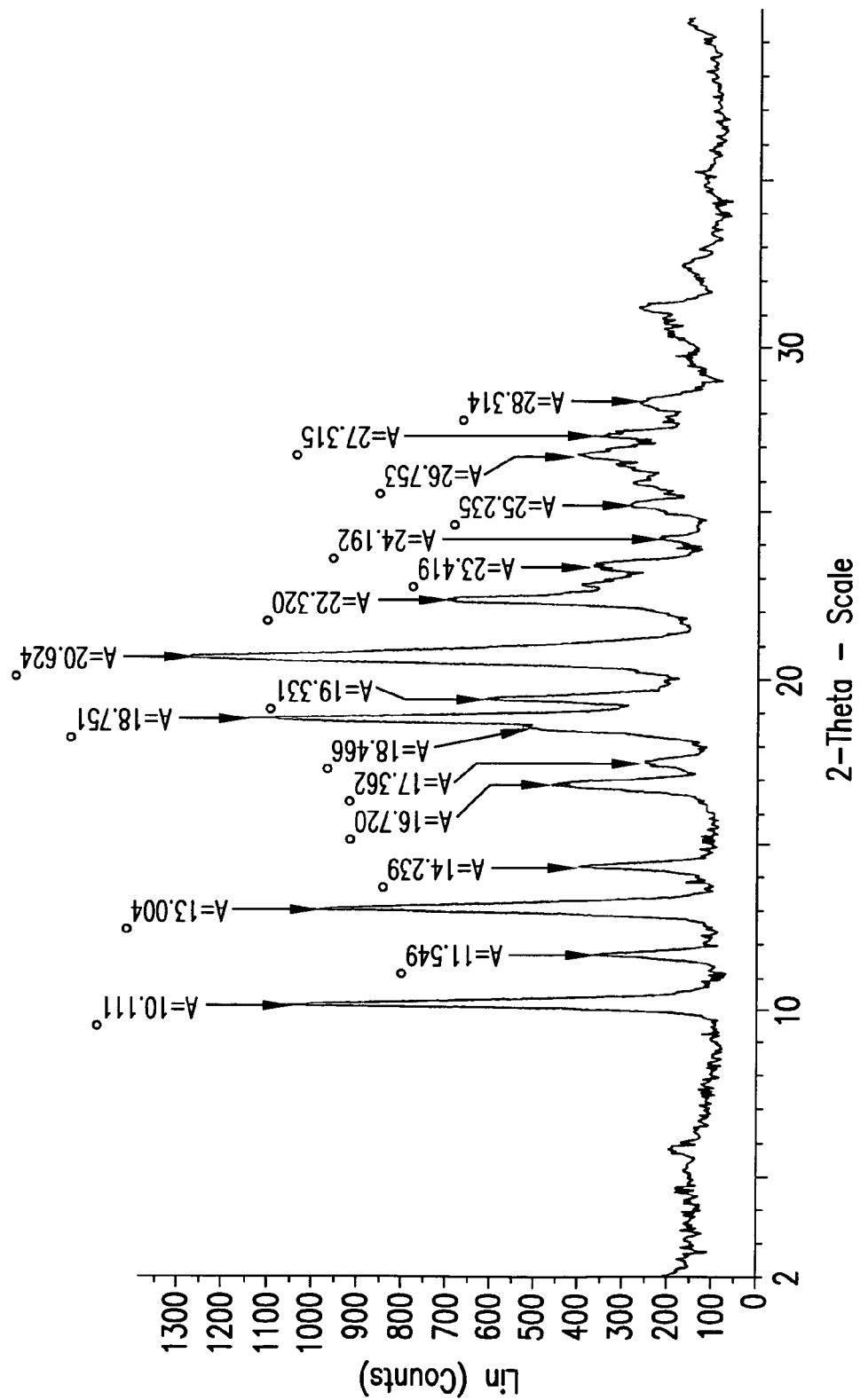
FIG. 4 illustrates a PXRD pattern of crystalline Varenicline Tosylate_form I obtained in example 3.
Figure 5:
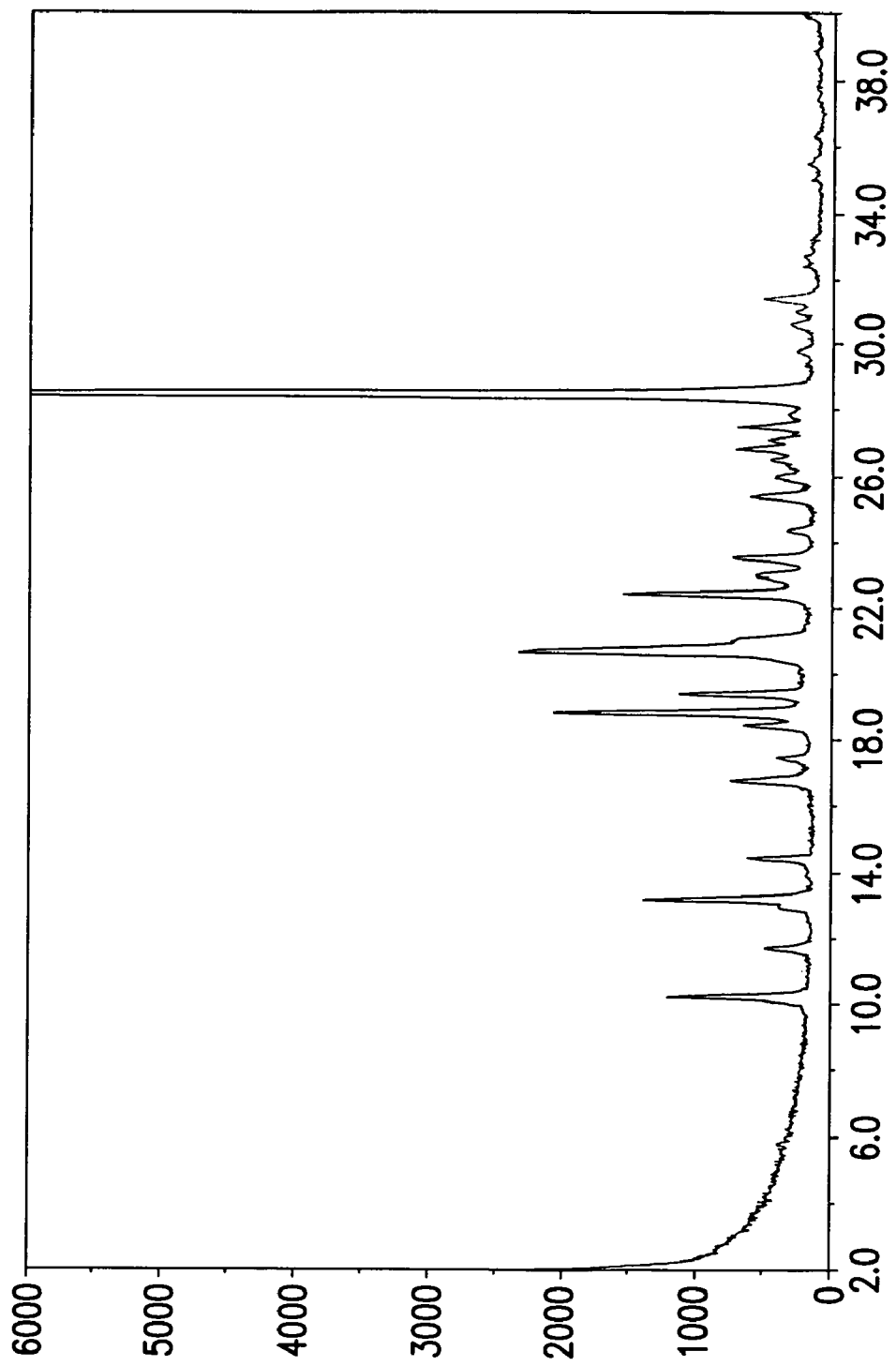
FIG. 5 illustrates a PXRD pattern of crystalline Varenicline Tosylate_form I obtained in example 6, where the peak at 28.45 degrees two theta is attributed to silicon.

The present invention provides a crystalline form of Varenicline Tosylate, designated form I, characterized by data selected from a group consisting of a powder XRD pattern having peaks at about 10.1, 13.0, and 18.7±0.2 degrees two theta and at least two peaks selected from the group consisting of 11.5, 14.2, 16.7, 19.3, and 20.6±0.2 degrees two theta, a powder XRD pattern having peaks at about 10.1, 13.0, 16.7, 18.7 and 20.6±0.2 degrees two theta, a powder XRD pattern having peaks at about 10.2, 13.1, 16.8, 19.4, 23.0±0.1 degrees two theta, a powder XRD pattern substantially as depicted in FIGS. 4 and 5, and combinations thereof. As noted above in the description of the drawings, FIG. 5 illustrates a powder XRD pattern of Varenicline Tosylate form I mixed with silicon, where the silicon is added as an internal standard, having a powder XRD peak corrected to be 28.45 degrees two theta.

The above crystalline form I may be further characterized by additional peaks selected from a group consisting of a powder XRD pattern having peaks at about 11.5, 14.2, 17.4, 19.3 and 22.3±0.2 degrees two theta, a powder XRD pattern having peaks at about 14.3, 18.5, 18.9, 23.5 and 26.8±0.1 degrees two theta and combinations thereof.

Crystalline form I of Varenicline Tosylate may be prepared by a process comprising combining Varenicline Base, a $C_1$-$C_6$ alcohol, and p-Toluene sulfonic acid to obtain a reaction mixture, and heating and then cooling the obtained reaction mixture.

Alternatively, crystalline form I of Varenicline Tosylate may be prepared by a process comprising heating a mixture of Varenicline Base in a $C_1$-$C_6$ alcohol and p-TSA, and further cooling the mixture.

Preferably, the alcohol used in the process described above is isopropyl alcohol (IPA) or methanol. Most preferably, it is methanol.

Heating in the process described above may be to a temperature of from about 65° C. to about 85° C., more preferably from about 65° C. to about 75° C., and more preferably from about 65° C. to about 70° C.

Cooling in the process described above is from a temperature of about 35° C. to about 0° C., more preferably, from about 35° C. to 15° C., and, more preferably, from about 32° C. to 28° C.

In one specific embodiment, Varenicline base in methanol is heated to a temperature of about 65° C. to about 70° C., p-TSA is added, and the mixture is then cooled to a temperature of about 28° C. to about 32° C.

Additionally, crystalline form I of Varenicline Tosylate may be prepared by heating crystalline form II of Varenicline Tosylate characterized below, for a period sufficient to convert form II to form I.

Heating of form II is to a temperature of about 25° C. to about 215° C. Preferably, heating is to about 100° C. to 215° C., more preferably to a temperature of about 80° C. to 210° C., and most preferably to about 210° C. Preferably, heating of form II is performed in a closed crucible of a Differential Scanning Calorimeter (DSC).

Figure 6:
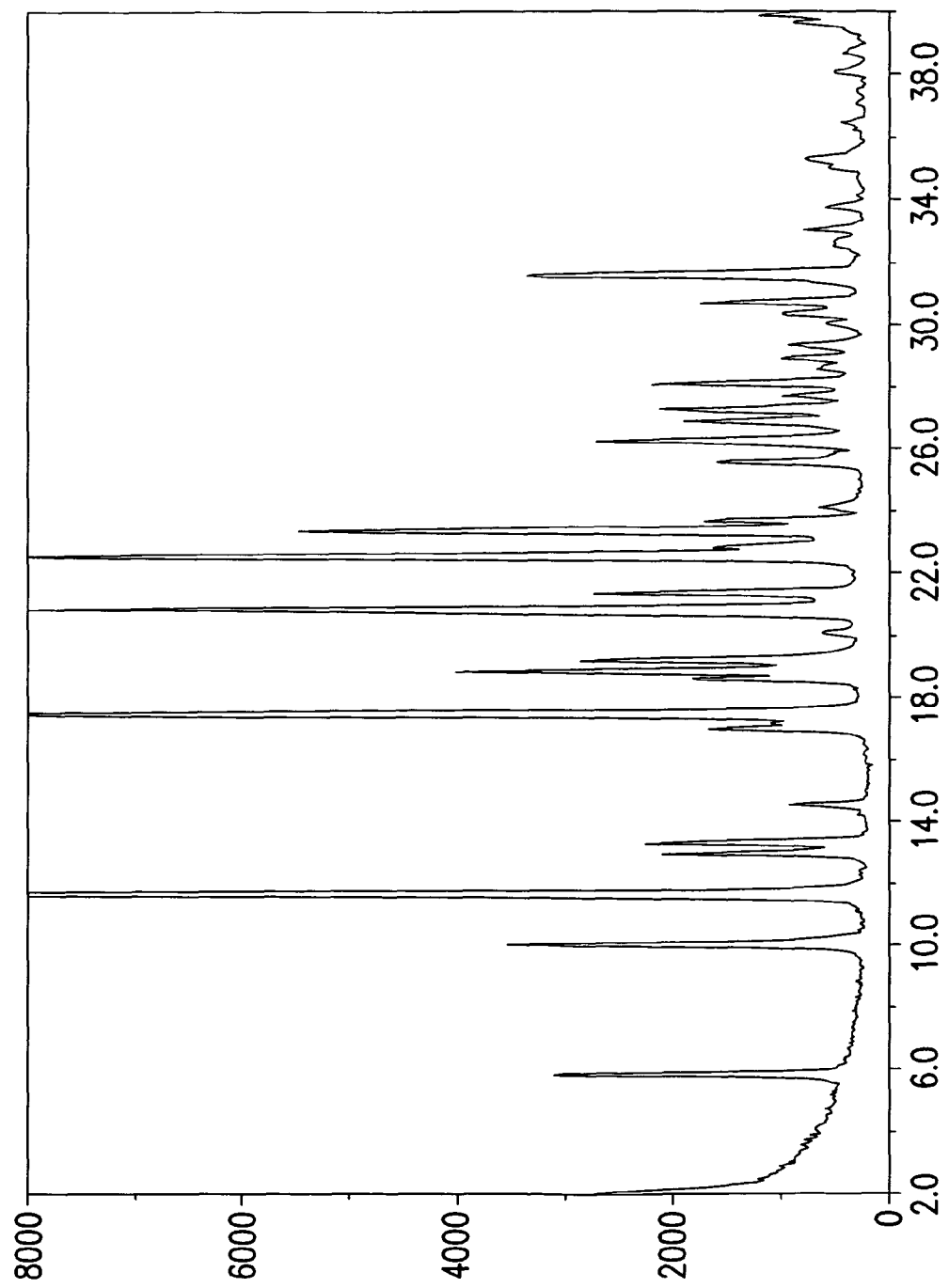
FIG. 6 illustrates a PXRD pattern of crystalline Varenicline Tosylate_form II obtained in example 7.
Figure 7:
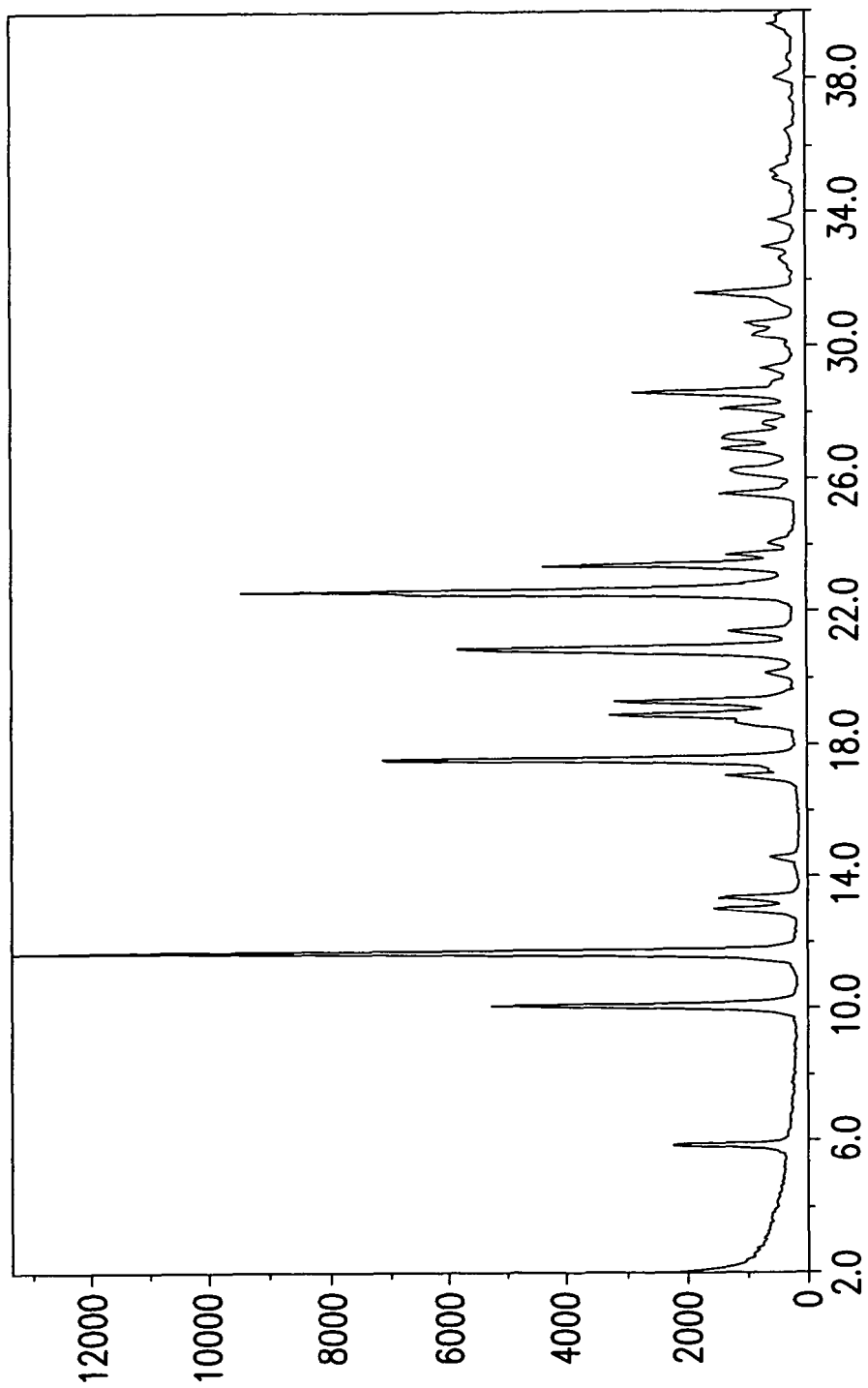
FIG. 7 illustrates a PXRD pattern of crystalline Varenicline Tosylate_form II, where the peak at 28.45 degrees two theta is attributed to silicon.

The present invention also provides a crystalline form of Varenicline Tosylate, designated form II, characterized by data selected from a group consisting of a powder XRD pattern having peaks at about 11.6, 12.9, 13.3, 20.8, and 21.3±0.2 degrees two theta, a powder XRD pattern having peaks at about 11.6, 12.9, 13.3, 21.3 and 23.3±0.2 degrees two theta, a powder XRD pattern having peaks at about 5.8, 10.0, 17.4, 19.1, 23.3±0.1 degrees two theta, a powder XRD pattern substantially as depicted in FIGS. 6 and 7 and combinations thereof. As noted above in the description of the drawings, FIG. 7 illustrates a powder XRD pattern of Varenicline Tosylate form II mixed with silicon, where the silicon is added as an internal standard, having a powder XRD peak corrected to be 28.45 degrees two theta.

The above crystalline form II may be further characterized by additional peaks selected from a group consisting of a powder XRD pattern having peaks at about 5.8, 10.0, 16.9, 17.4, and 18.8±0.2 degrees two theta, a powder XRD pattern having peaks at about 11.5, 13.2, 20.8, 22.5 and 25.4±0.1 degrees two theta, and combinations thereof.

Crystalline form II of Varenicline Tosylate may be prepared by a process comprising; combining Varenicline Base, methanol, a $C_6$-$C_{12}$ aromatic hydrocarbon, and p-Toluene sulfonic acid to obtain a reaction mixture, and heating and cooling the obtained reaction mixture.

Alternatively, crystalline form II of Varenicline Tosylate may be prepared by a process comprising heating a mixture of Varenicline base in methanol, $C_6$-$C_{12}$ aromatic hydrocarbon, and p-TSA, and cooling the mixture.

The $C_6$-$C_{12}$ aromatic hydrocarbon used in the process described above can be toluene or xylene (can be used is a form of meta-xylene, ortho-xylene, para-xylene and mixtures thereof). More preferably, toluene is used.

Varenicline base is preferably used in a mixture of about 15 percent to about 30 percent volume $C_6$-$C_{12}$ aromatic hydrocarbon and about 70 percent to about 85 percent volume methanol.

Heating in the process described above may be to a temperature of from about 65° C. to about 70° C.

Cooling in the process described above is from a temperature of about 30° C. to about 20° C.

Figure 8:
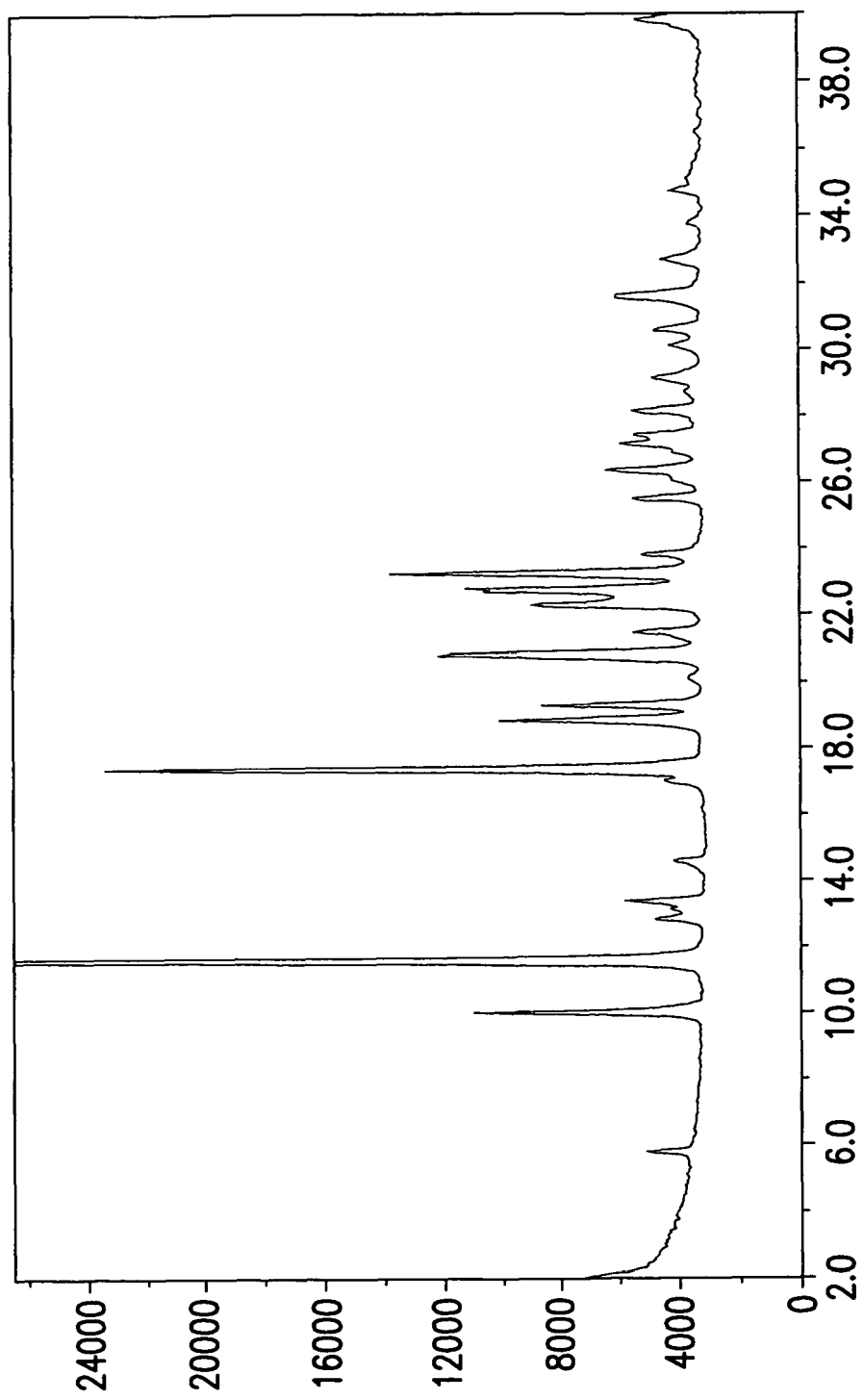
FIG. 8 illustrates a PXRD pattern of crystalline Varenicline Tosylate_form III obtained in example 8.
Figure 9:
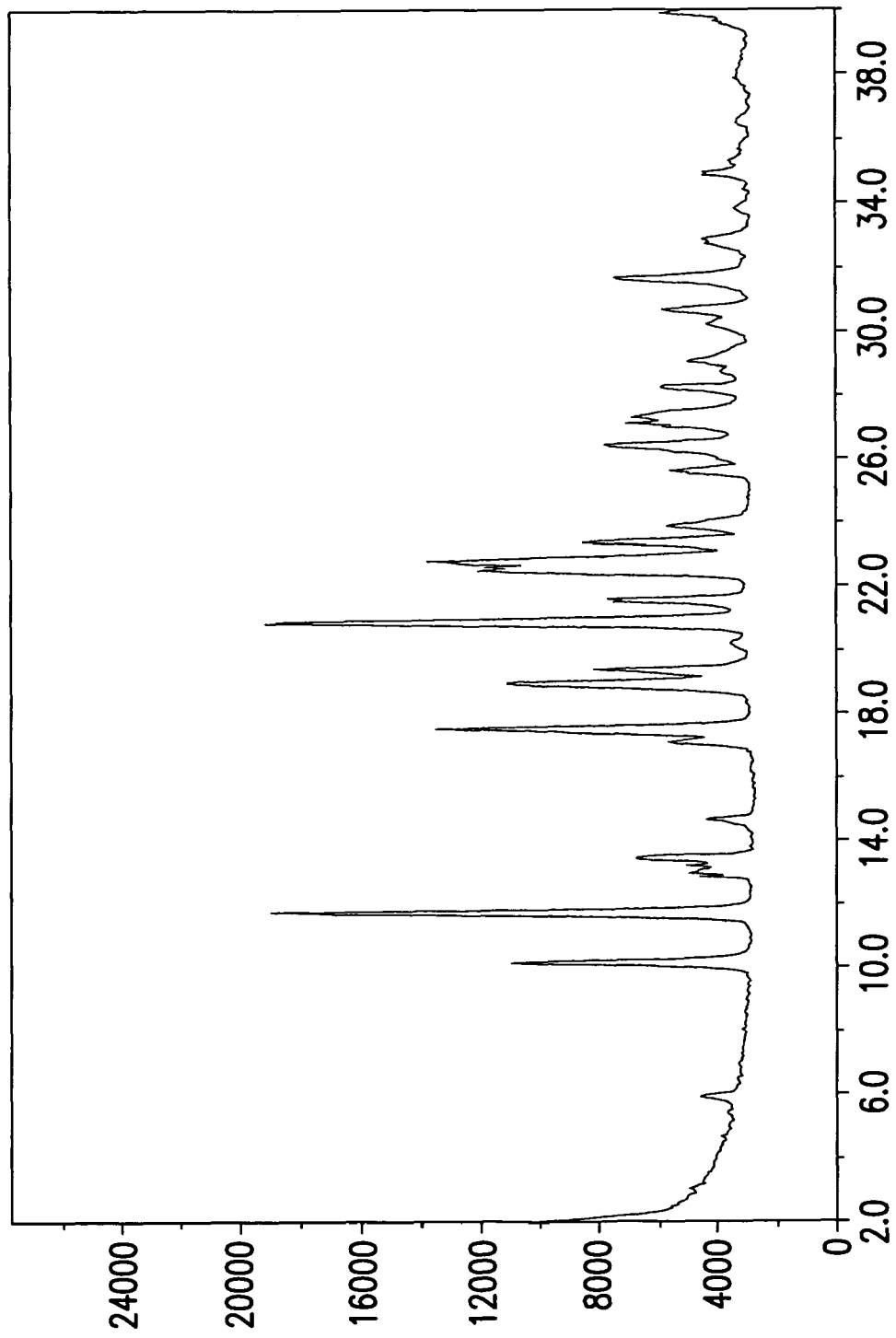
FIG. 9 illustrates a PXRD pattern of crystalline Varenicline Tosylate_form III obtained in example 9.
Figure 10:
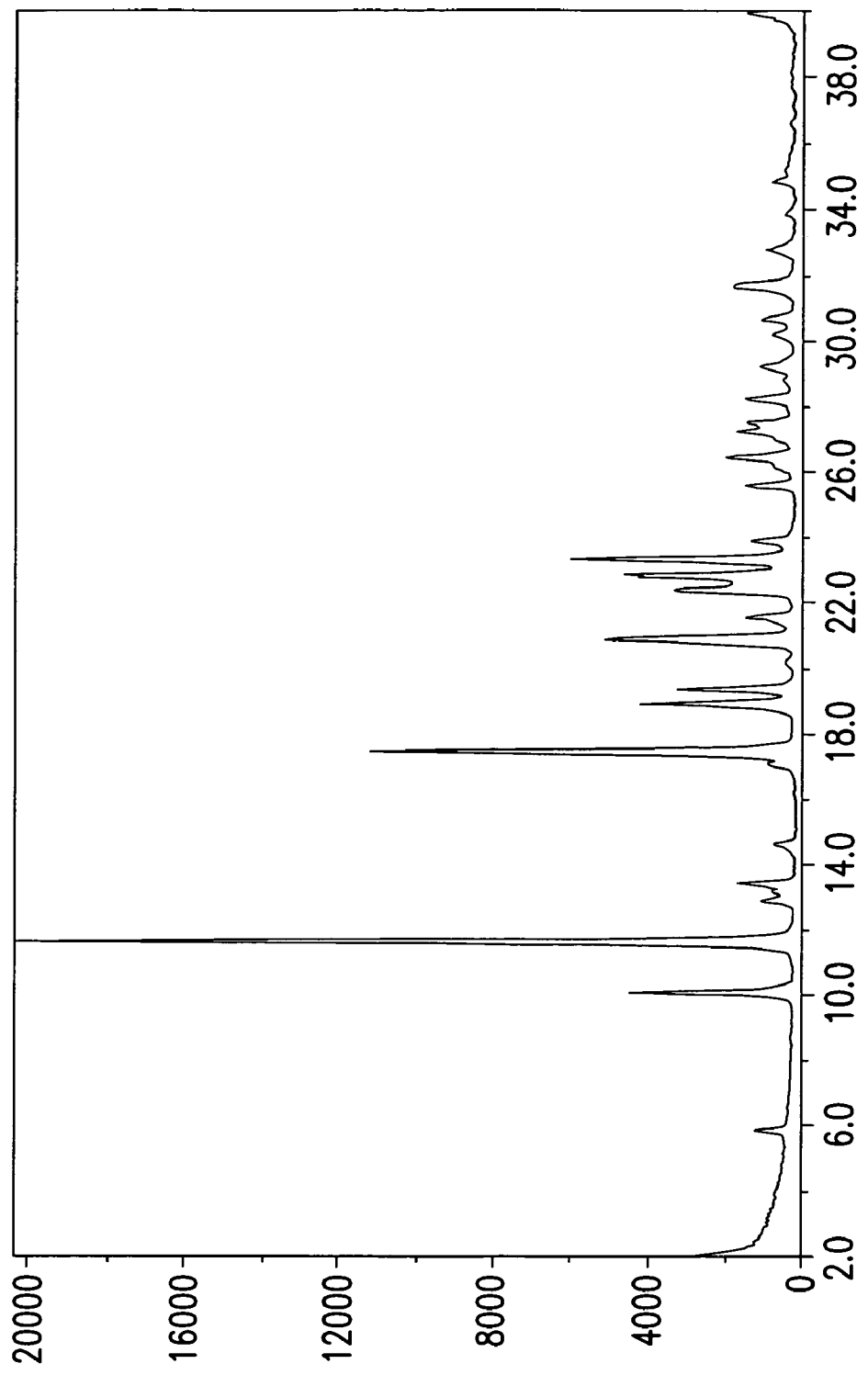
FIG. 10 illustrates a PXRD pattern of crystalline Varenicline Tosylate_form III obtained in example 10.

The present invention also provides a crystalline form of Varenicline Tosylate, designated form III, characterized by a powder XRD pattern having peaks at about 10.0, 11.6, 17.4, 22.3, and 22.8±0.2 degrees two theta and additional peaks at about 5.8, 18.8, 19.3, 20.8, and 23.2±0.2 degrees two theta, as depicted in the PXRD diffraction of FIGS. 8, 9 and/or 10. As noted above in the description of the drawings, FIG. 10 illustrates a powder XRD pattern of Varenicline Tosylate form III mixed with silicon, where the silicon is added as an internal standard, having a powder XRD peak corrected to be 28.45 degrees two theta.

In particular, Varenicline Tosylate form III can be characterized by a powder XRD pattern having peaks at about 10.0, 11.6, 17.4, 22.3, and 22.8±0.2 degrees two theta.

The Varenicline Tosylate form III described above can be further characterized by data selected from the group consisting of a powder XRD pattern having peaks at about 5.8, 18.8, 19.3, 20.8, and 23.2±0.2 degrees two theta, a powder XRD pattern having peaks at about 5.9, 18.9, 19.3, 20.8 and 26.4±0.2 degrees two theta and combinations thereof.

The present invention also provides a process for preparing Varenicline Tosylate form III, comprising exposing Varenicline Tosylate form II to less than about 5 percent relative humidity, for a period sufficient to convert form II to form III.

The relative humidity used in the process described above is preferably 0 percent.

As used herein, a "sufficient" period necessary to obtain a desired polymorphic form can be determined by periodically measuring a sample by powder XRD until the desired polymorphic form is obtained.

Preferably, Varenicline Tosylate is exposed in the above process to 0 percent relative humidity for a period of about 1 to about 15 days, more preferably, for about 1 to about 10 days, more preferably, for about 1 to about 7 days, and, most preferably, 2 days.

The above process is preferably performed at room temperature.

The present invention also provides a process for preparing Varenicline Tosylate form III by heating Varenicline Tosylate form II for a period sufficient to convert form II to form III.

The heating described in the process above is preferably to a temperature of about 70° C. to about 100° C., more preferably, to about 75° C. to about 85° C., and, more preferably, to about 80° C.

Preferably, the Varenicline Tosylate is heated for a period of about half an hour to about two hours, more preferably for about one hour.

Figure 11:
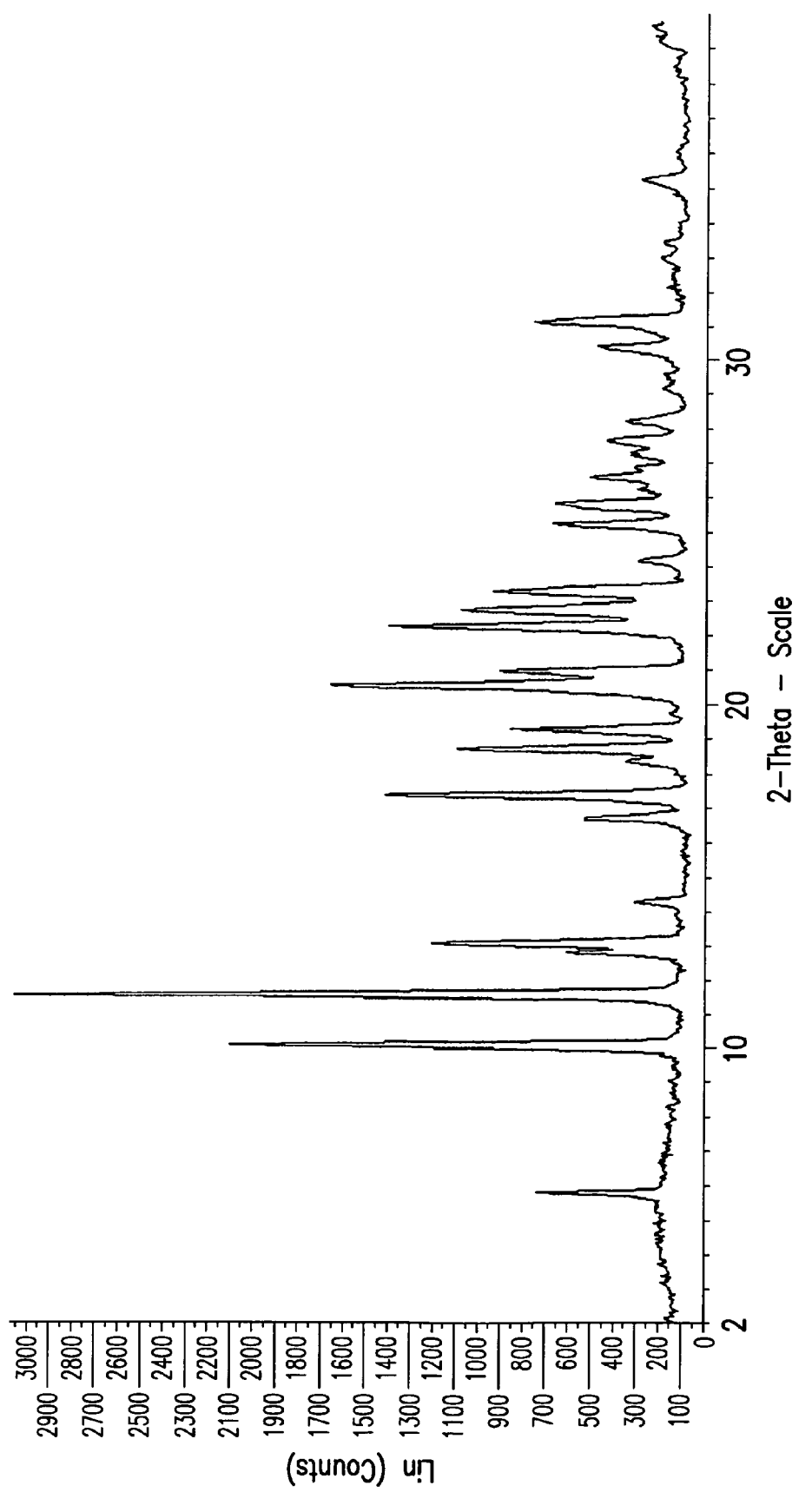
FIG. 11 illustrates a PXRD pattern of crystalline Varenicline Tosylate_form IV obtained in example 11.
Figure 12:
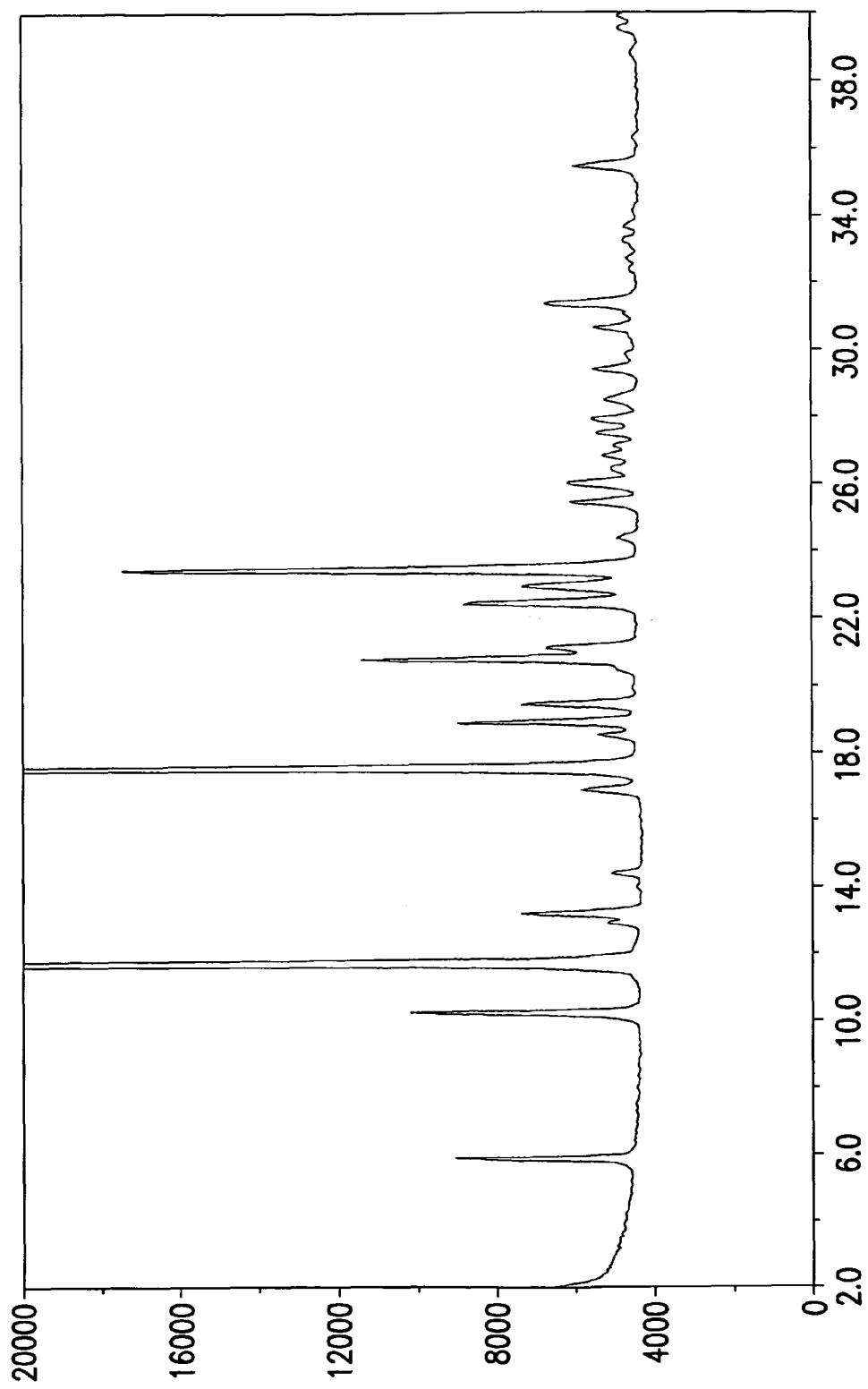
FIG. 12 illustrates a PXRD pattern of crystalline Varenicline Tosylate_form IV obtained in example 12.
Figure 13:
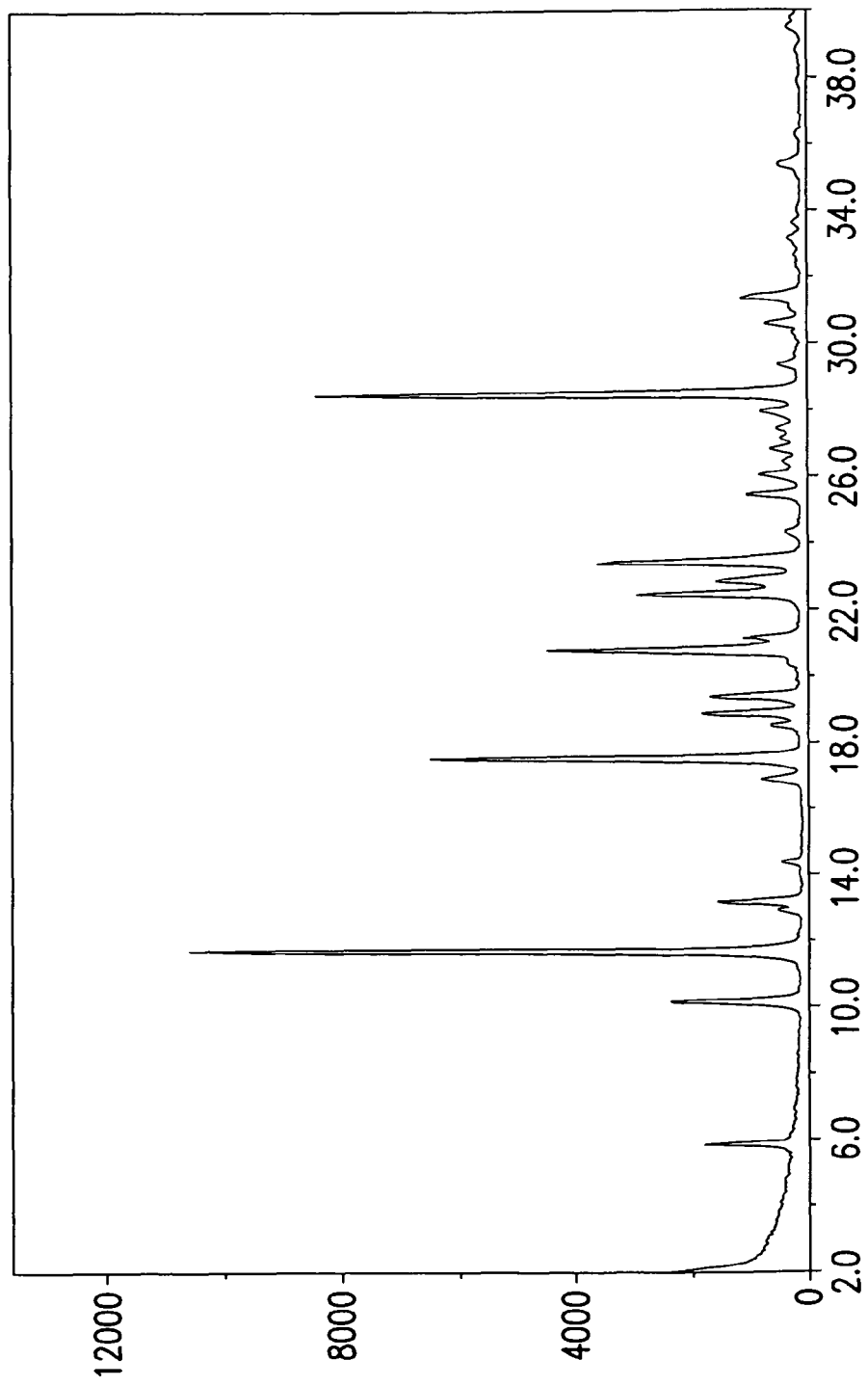
FIG. 13 illustrates a PXRD pattern of crystalline Varenicline Tosylate_form IV obtained in example 14, where the peak at 28.45 degrees two theta is attributed to silicon.

The present invention also provides a crystalline form of Varenicline Tosylate, designated form IV, characterized by a powder XRD pattern having peaks at about 11.6, 13.2, 19.5, 23.0, and 24.4±0.2 degrees two theta and additional peaks at about 10.3, 16.9, 18.9, 20.7 and 22.5±0.2 degrees two theta as depicted in the PXRD diffraction of FIGS. 11 and 12. As noted above in the description of the drawings, FIG. 12 illustrates a powder XRD pattern of Varenicline Tosylate form IV mixed with silicon, where the silicon is added as an internal standard, having a powder XRD peak corrected to be 28.45 degrees two theta.

In particular, Varenicline Tosylate form IV can be characterized by a powder XRD pattern having peaks at about 11.6, 13.2, 19.5, 23.0, and 24.4±0.2 degrees two theta.

The Varenicline Tosylate form IV described above can be further characterized by a powder XRD pattern having peaks at about 10.3, 16.9, 18.9, 20.7, and 22.5±0.2 degrees two theta.

The present invention provides a process for preparing Varenicline Tosylate form IV, comprising combining Varenicline base, a $C_1$-$C_6$ alcohol, a $C_1$-$C_3$ halogenated aliphatic hydrocarbon, and p-Toluene sulfonic acid (p-TSA) to obtain a reaction mixture, and heating and then cooling the obtained reaction mixture.

Preferably, the $C_1$-$C_6$ alcohol used in the process described above is isopropyl alcohol (IPA) or methanol. Most preferably, it is methanol.

Preferably, the $C_1$-$C_3$ halogenated aliphatic hydrocarbon is methylene di-chloride (MDC) or ethylene dichloride. Most preferably, it is MDC.

Heating in the process described above may be to a temperature of from about 65° C. to about 85° C., more preferably, from about 65° C. to about 75° C., and, most preferably, from about 65° C. to about 70° C.

Cooling in the process described above is from a temperature of about 35° C. to about 10° C., more preferably, from about 35° C. to 20° C., and, most preferably, from about 30° C. to 25° C.

The present invention also provides a process for preparing Varenicline Tosylate form IV, comprising wetting Varenicline Tosylate form II with water, and grinding the wetted material.

As used herein, 'wetting' refers to damping about 100 mg to about 200 mg Varenicline Tosylate with about 1 to about 2 drops of water, where a drop of water refers to about 0.1 ml to about 0.25 ml of water.

Preferably, the wet Varenicline Tosylate is ground for a period of about 1 minute to about 5 minutes, and, more preferably, for about 1 minute.

Preferably, the wet Varenicline Tosylate is ground using a mortar and pestle. The time frame and equipment used for grinding can be modified for use on industrial scale.

The present invention also provides a process for preparing Varenicline Tosylate form IV, comprising exposing Varenicline Tosylate form II to a relative humidity of from about 80 percent to about 100 percent for a period sufficient to convert form II to form IV.

Preferably, the exposure in the above process was performed for a period of about 1 to about 15 days. more preferably, for about 1 to about 10 days, more preferably for about 1 to about 7 days, and most preferably, 1 day.

In one specific embodiment, Varenicline Tosylate form II is exposed to a relative humidity of about 100 percent for a period of about 1 day at room temperature to obtain Varenicline Tosylate form IV.

As used herein, "pure Varenicline Tosylate" or "pure Varenicline Base" refers to total chemical purity of Varenicline Tosylate/Base as measured by area HPLC.

In one embodiment, the present invention encompasses pure Varenicline Tosylate.

Preferably, the Varenicline Tosylate obtained according to any of the processes described above has a total purity of greater than 97 percent by area HPLC. More preferably, greater than 99 percent. Most preferably, the Varenicline Tosylate has a total purity of 99.99 percent by area HPLC.

A repetition of U.S. Pat. No. 6,410,550 Example 26C, with the exception of an additional extraction with MDC, provided Varenicline base having a total purity of 96.3 percent. The present invention provides a process for obtaining pure Varenicline Tosylate, having a purity greater than 97 percent, or greater than 98 percent, or greater than 99 percent, which is further converted to pure Varenicline base. We observed that the present invention allows obtaining Varenicline base with a total purity of greater than 99.9 percent.

In particular, it has been found that Varenicline Tosylate formed from Varenicline base has a higher purity than the Varenicline base starting material, and the conversion of the Varenicline Tosylate back to Varenicline base provides a Varenicline base having a higher purity than the Varenicline base starting material.

Therefore, the present invention encompasses pure Varenicline base.

The present invention provides a process for obtaining pure Varenicline base, comprising slurrying Varenicline Tosylate in water with a base and an inert organic solvent. Preferably, the Varenicline Tosylate used to produce the Varenicline base is first prepared from Varenicline base.

Alternatively, the present invention provides a process for obtaining pure Varenicline base, comprising combining Varenicline Tosylate in the presence of a base and an inert organic solvent, or mixtures thereof.

The water used in the process described above is preferably Demineralized water (DM water).

Preferably, the Varenicline base obtained according to the purification process described above has a total purity of greater than 97 percent or 98 percent by area HPLC, more preferably greater than 99 percent by area HPLC. Most preferably, the total purity is 99.97 percent.

Not to be limited to any mechanism, the above reaction mixture leads to phase separation of organic and aqueous phases. Preferably, Varenicline base may be recovered from the organic phase.

Optionally, Varenicline base obtained in the process described above is further precipitated from the reaction mixture using an organic solvent.

The precipitating organic solvent described above is a $C_5$-$C_9$ alkane. Preferably the solvent is selected from a group consisting of pentane, hexane, and heptane. Most preferably, n-heptane is used.

Preferably, the Varenicline Tosylate used in the purification process described above, has a total purity of above 97 percent by area HPLC, more preferably above 99 percent. Most preferably, it is 99.99 percent The base used in the purification process described above is selected from the group consisting of alkali metal and alkaline earth metal carbonates, hydroxides, organic bases, and aqueous ammonia. More preferably, the base is selected from lithium carbonate, sodium carbonate, sodium bicarbonate, potassium carbonate, sodium hydroxide, and potassium hydroxide; $C_1$-$C_4$ alkyl amine, such as triethyl amine, diisopropyl amine, and diisopropyl ethyl amine; di- and tri-hydroxy $C_1$-$C_4$ alkyl amine; morpholine, piperidine, pyridine and pyrrolidine, and aqueous ammonia. Preferably, the base is selected from the group consisting of lithium carbonate, sodium carbonate, sodium bicarbonate, potassium carbonate, sodium hydroxide, potassium hydroxide, and aqueous ammonia. Most preferably, the base is aqueous ammonia.

The inert solvent used in the process described above is selected from the group consisting of $C_6$-$C_8$ aromatic hydrocarbons, $C_4$-$C_6$ esters, and $C_1$-$C_2$ halogenated hydrocarbons. Preferably, the solvent is selected from the group consisting of xylene, which can be in the form of meta-xylene, ortho-xylene, para-xylene, and mixtures thereof, benzene, toluene, butyl acetate, isopropyl acetate, ethyl acetate, ethylene dichloride, methylene dichloride (MDC), carbon tetra chloride, chloroform, and combinations thereof. Most preferably, the inert solvent is MDC.

The reaction mixture in the process described above is preferably maintained at a temperature of about 20° C. to about 60° C. More preferably, the temperature is between about 20° C. to about 40° C. Preferably, the reaction mixture in the above process is stirred for a period of about half an hour to about 2 hours, and, more preferably, at a temperature of about 25° C. to about 30° C.

Varenicline Tosylate can be combined with water and a base such as those described above. Preferably, first a solution of Varenicline Tosylate in water is prepared, followed by addition of the base to obtain a slurry. Varenicline can then be extracted into a water immiscible solvent. Examples of water immiscible solvents include $C_6$-$C_8$ aromatic hydrocarbons, $C_4$-$C_6$ esters and $C_1$-$C_2$ halogenated hydrocarbons. Preferably, the solvent is selected from the group consisting of xylene (can be used is a form of meta-xylene, ortho-xylene, para-xylene, and mixtures thereof), benzene, toluene, butyl acetate, isopropyl acetate, ethyl acetate, ethylene dichloride, methylene dichloride (MDC), carbon tetra chloride, chloroform, and combinations thereof. Most preferably, MDC is used.

In one specific embodiment, 30 percent aqueous sodium hydroxide solution is added to a solution of Varenicline Tosylate in DM water, further combined with toluene, and maintained at a temperature of 50° to 60° C. for 30 minutes. Varenicline base is then extracted from the reaction mixture using toluene and n-heptane is added in order to precipitate Varenicline base as a solid material.

The present invention also provides a process for preparing Varenicline L-Tartrate, comprising preparing Varenicline Tosylate according to any of the processes described above, and converting the Varenicline Tosylate to Varenicline L-Tartrate. Preferably, the conversion of the Varenicline Tosylate to Varenicline L-Tartrate comprises converting the Varenicline Tosylate to Varenicline base according to any of the processes described above. Conversion of Varenicline base to Varenicline L-Tartrate may be obtained according to methods known in the art, such as the one described in U.S. Pat. No. 6,890,927, incorporated herein by reference, wherein L-tartaric acid in methanol is combined with Varenicline base in methanol.

Varenicline base used in any of the processes described above may be obtained according to any known method in the art, such as the one described in U.S. Pat. No. 6,410,550, incorporated herein by reference, or according to examples 1 or 2 of the present application, wherein 1-(5,8,14-Triazatetracyclo[10.3.1.0$^{2,11}$.0$^{4,9}$]hexadeca-2(11),3,5,9-pentaene)-2,2,2-trifluoro-ethanone in methanol is reacted with a base, e.g., alkali metal, alkaline earth metal carbonates or hydroxides, and then heated.

Having described the invention with reference to certain preferred embodiments, other embodiments will become apparent to one skilled in the art from consideration of the specification. The disclosures of the references referred to in this patent application are incorporated herein by reference. The invention is further defined by reference to the following examples describing in detail the process and compositions of the invention. It will be apparent to those skilled in the art that many modifications, both to materials and methods, may be practiced without departing from the scope of the invention.

EXAMPLES

NMR Analysis

NMR spectra were taken on a Bruker Avance DRX 400 MHz (frequency for $^1$H 400 MHz and for $^{13}$C 100.61 MHz) in DMSO-$d_6$ solution at 398K.
HPLC Methodology for the Impurity Profile:
Preparation of Buffer:
0.02M Ammonium Acetate and adjusted pH 9.0 with 10 percent ammonia solution. pH was measured with a pH meter (Model no. Cyber scan 510, PC)
Preparation of Mobile Phase:
Mixture 70 percent of Buffer and 30 percent of Methanol (70:30), v/v)
Chromatographic Conditions:
Column: X terra RP-18, 150*3.9 mm, 5 μm
Flow: 0.5 ml/min
Injection Volume: 5.0 μl
Detector: 235 nm
Run time: 20 mins
Column Temperature: 30° C.
Diluent: Buffer:methanol (70:30 v/v)
Autosampler temperature: 10° C.
XRD
Form I was analyzed on a Bruker X-Ray powder diffractometer Cu-tube, model D8 advance equipped with lynxEye position sensitive detector or equivalent. Measurements were taken at a wavelength of Kα=1.5406 Cu
Sample holder: a standard sample holder of PMMA. (In case of low amount of material, standard sample holder of PMMA was used with zero background plate).
Scanning Parameters:
Sample: Spin mode, rotation speed: 60 rpm.
Range: 2-40 degrees two-theta.
Scan mode: Continuous scan.
Step size: 0.05±0.005 deg.
Time/Step: 0.1 sec.
Divergon slit: 1
Procedure:
Sample preparation—Gently grind a small amount of powder in an agate mortar with the pestle. Fill the powder in the round cavity of the sample holder by pressing with a glass plate or equivalent, to form a smooth surface that its height will not deviate from the sample holder's height.

In the powder XRD measurements taken with silicon mixed with the Varenicline Tosylate, the peak positions were calibrated using silicon powder as an internal standard in the admixture when the powder XRD of the sample was measured. The position of the silicon (111) peak was corrected to be 28.45 degrees two theta. The positions of Varenicline Tosylate forms I, II and IV peaks were corrected respectively. No correction was performed on the diffractograms presented in the figures.

Forms II-IV were analyzed on an ARL (Scintag) X-ray powder diffractometer model X'TRA-019, Peltier detector, having a round standard aluminum sample holder with a round, zero background quartz plate. The cathode is CuKa radiation, λ=1.5418 Å.

Scanning parameters for measuring Forms II-IV without silicon and Form IV with silicon: Range: 2-40 deg. 2 theta, continuous Scan, Rate: 3 deg/min, Step Size: 0.05. The accuracy of peal: positions is defined as +/−0.2 degrees.

Scanning parameters for Form I with silicon: Range: 2-40 deg. 2 theta, continuous Scan, Rate: 1 degree/minute, Step Size: 0.02. The accuracy of peak positions is defined as +/−0.1 degrees.

Scanning parameters for measuring Form II with silicon: Range: 2-40 degrees 2 theta, continuous Scan, Rate: 3 deg/min, Step Size: 0.05. The accuracy of peak positions is defined as ±0.1 degrees.

Preparation of 5,8,14-Triazatetracyclo[10.3.1.0²,¹¹.0⁴,⁹]hexadeca-2(11),3,5,7,-9-pentaene (Varenicline Base) (Comparative Example to U.S. Pat. No. 6,410,550 Example No. 26C, with an Extra MDC Extraction, Up to Reaction with HCL)

Example 1

A suspension of 1-(5,8,14-Triazatetracyclo[10.3.1.0²,¹¹.0⁴,⁹]hexadeca-2(11),3,5,9-pentaene)-2,2,2-trifluoro-ethanone (4.0 g) (VRN 11) {HPLC purity 89.97%} in methanol was treated with an aqueous solution of sodium carbonate (2.76 g in 25 ml water). The mixture was warmed to 70° C. for 2 hours, and the progress of the reaction was monitored by TLC (MDC:MeOH 9:1). The solvent was distilled under vacuum at 55-60° C. to obtain an oily product, which was dissolved in water (250 ml). The above mixture was cooled to 25-30° C., extracted with MDC (4×125 ml), and the aqueous layer was separated. The combined organic layer was filtered through a cotton plug, and concentrated to obtain an oily product, i.e. 5,8,14-Triazatetracyclo[10.3.1.0²,¹¹.0⁴,⁹]hexadeca-2(11),3,5,7,9-pentaene (VRN-BASE) (Yield-1.92 g (72.67% (relative to VRN-11)), HPLC purity-96.3%,), which solidifies on standing.

Preparation of 5,8,14-Triazatetracyclo[10.3.1.0²,¹¹.0⁴,⁹]hexadeca-2(11),3,5,7,-9-pentaene (Varenicline Base) (Reference Example)

Example 2

A suspension of 1-(5,8,14-Triazatetracyclo[10.3.1.0²,¹¹.0⁴,⁹]hexadeca-2(11),3,5,9-pentaene)-2,2,2-trifluoro-ethanone (20 g) (HPLC purity not lower than (NTL) 98%) in methanol (120 ml) was treated with an aqueous solution of sodium carbonate (13.8 g in 125 ml water). The mixture was warmed to 65° to 70° C. for 3 hours, and the reaction was monitored by HPLC. The methanol was completely distilled out under vacuum. The residue was dissolved in water (200 ml). The reaction mass was cooled to 25° to 30° C., and extracted with MDC (5×100 ml.). The combined organic layer washed with DM water (2×100 ml). The organic layer was concentrated to the obtain product, i.e. Varenicline Base (Yield 12 g (87.20% (relative to VRN-11)), HPLC Purity NLT 98%).

Preparation of 5,8,14-Triazatetracyclo[10.3.1.02,11.04,9]hexadeca-2(11),3,5,7,9-pentaene Tosylate (Varenicline Tosylate) Form I Example 3

A mixture of Isopropyl alcohol (1000 ml) and 5,8,14-Triazatetracyclo[10.3.1.0²,¹¹.0⁴,⁹]hexadeca-2(11),3,5,7,9-pentaene (Varenicline Base (VRN Base), having a total purity of 96.89%) (100 g) was charged into the reactor at 25-30° C. The obtained mixture was heated to 75-80° C. and maintained at this temperature for 15 minutes. Then, p-Toluene sulfonic acid (p-TSA) (108.13 g) was added at 70-75° C., and the mixture was stirred for additional 15 minutes. The obtained reaction mass was cooled to 0-5° C., and maintained at this temperature for 1 hour.

The obtained solid was filtered and washed with chilled (0-5° C.) isopropyl alcohol (700 ml), and dried under vacuum at 50-55° C. to obtain 5,8,14-Triazatetracyclo[10.3.1.0²,¹¹.0⁴,⁹]hexadeca-2(11),3,5,7,9-pentaene Tosylate that has an HPLC purity-of 98.74%. Yield: 1.4-1.5 w/w (81.84% (relative to VRN-Base)).

Example 4

A suspension of 5,8,14-Triazatetracyclo[10.3.1.02,11.04,9]hexadeca-2(11),3,5,7,9-pentaene (Varenicline Base, having a total purity of 98.65%) (10 g) in isopropyl alcohol (100 ml) was treated with p-TSA (10.8 g) at 70-75° C. The mixture was stirred at 75-80° C. for 30 minutes, slowly (within one hour) cooled to 28-32° C., and maintained for 2 hours. The crystallized solid was filtered, and the wet cake was washed with isopropyl alcohol (25 ml×2). The product was then dried under vacuum at 50-55° C. for 10-15 hours. (Yield 13 g (68.78% (relative to VRN-Base)), HPLC purity 99.42%)

Example 5

A suspension of 5,8,14-Triazatetracyclo[10.3.1.0²,¹¹.0⁴,⁹] hexadeca-2(11),3,5,7,9-pentaene (Varenicline Base, having a total purity of 99.18%) (120 g) in Methanol (600 ml) was treated with para-toluene sulfonic acid (129.8 g) at 25-30° C. The mixture was stirred at 65-70° C. for 60 minutes, and the reaction mass was slowly (for a period of 30 to 45 minutes) cooled to 28-32° C., and maintained for 2 hours. The crystallized solid was filtered, and the wet cake was washed with Methanol (120 ml). The product was dried under vacuum at 50-55° C. for 10-12 hours. (Yield 171.9 g (64.41% (relative to VRN-Base)), HPLC purity 99.95%)

Example 6

About 10 mg of Varenicline Tosylate form II was placed in closed crucible with three holes of the Differential Scanning Calorimeter (DSC) [Mettler Toledo DSC 821$^e$ calorimeter] The sample was heated to 210° C. (at a heating rate of 10° C./min). The sample was left to cool done to room temperature, and a powder XRD analysis was preformed. According to powder XRD diffractogram, Varenicline Tosylate form I was obtained.

Preparation of 5,8,14-Triazatetracyclo[10.3.1.02,11.04,9]hexadeca-2(11),3,5,7,9-pentaene Tosylate (Varenicline Tosylate) Form II Example 7

To a clean and dry round bottom flask were charged methanol (600 ml) and 1-(5,8,14-Triazatetracyclo[10.3.1.0²,¹¹.0⁴,⁹]hexadeca-2(11),3,5,9-pentaene)-2,2,2-trifluoro-ethanone, having a total purity of 98.43% (100 g), at 20-30° C. To this suspension was added aqueous sodium hydroxide solution (26 g in 600 ml DM water) at 20-30° C. in 1 hour. The reaction mixture was maintained for 1 hour at 20-30° C., and the progress of the reaction was monitored by HPLC. After completion of the reaction, the temperature was raised to 50-60° C., and a methanol and water (600 ml) mixture was distilled out under vacuum (50-100 mm Hg) at 50-60° C. To the residue was added toluene (500 ml) at 50-60° C., the mixture was maintained with stirring for 30 minutes, and the layers were separated at 50-60° C. The aqueous layer was extracted with toluene (4×500 ml) at 50-60° C. The combined organic layer was distilled under vacuum at 50-60° C. leaving 100 ml of toluene with the product. To the residue was added methanol (200 ml) at 45-55° C., and the mixture of toluene and methanol (200 ml) was distilled out under vacuum (50-

100 mm Hg) at 50-60° C. To the residue was charged methanol (200 ml) 45-55° C., and the mixture of toluene and methanol (200 ml) was distilled out under vacuum (50-100 mm Hg) at 50-60° C. To the residue were added methanol (140 ml), activated charcoal (6 g), and neutral aluminum oxide (6 g) at 45-55° C., and the mixture was heated to 65-70° C. and maintained for 1 hour. The resultant mixture was cooled to 45-55° C., and filtered through a celite bed (20 g). The celite bed was washed with methanol (60 ml). To the filtrate obtained was charged p-toluene sulfonic acid (66 g) in organic layer at 45-55° C., and maintained for 15 minutes. The temperature was raised to 65-70° C., and maintained for 1 hour. The resultant mixture was cooled to 20-30° C., and maintained for 2 hours. The solid crystallized was filtered at 20-30° C., and the wet cake was washed with methanol (60 ml). The obtained product was dried under vacuum at 45-55° C.

Yield: 0.85-0.95 w/w (72.94% (relative to VRN-11)). HPLC purity-99.88%.

Preparation of 5,8,14-Triazatetracyclo[10.3.1.0$^{2,11}$.0$^{4,9}$]hexadeca-2(11),3,5,7,9-pentaene Tosylate (Varenicline Tosylate) Form III Example 8

About 200 mg of Varenicline Tosylate (Form II) was exposed to 0 percent relative humidity (RH) for 7 days at room temperature. The resulting solid was analyzed by XRD, and shown to be a new Form (Form III).

Example 9

About 200 mg of Varenicline Tosylate (Form II) was heated to 80° for one hour in an oven. The resulting solid was analyzed by XRD, and shown to be a new Form (Form III).

Example 10

About 200 mg of Varenicline Tosylate Form II entered to humidity cell of 0% relative humidity for 2 days. The resulted material was measured by XRD. According to XRD pattern Form III was obtained Preparation of 5,8,14-Triazatetracyclo[10.3.1.0$^{2,11}$.0$^{4,9}$]hexadeca-2(11),3,5,7,9-pentaene Tosylate (Varenicline Tosylate) Form IV Example 11

A suspension of 1-(5,8,14-Triazatetracyclo[10.3.1.0$^{2,11}$.0$^{4,9}$]hexadeca-2(11),3,5,9-pentaene)-2,2,2-trifluoroethanone (VRN-11) (200 gm) (HPLC purity not lower than (NLT) 98%) in methanol (1200 ml) was treated with an aqueous solution of sodium carbonate (138.1 gm in 1250 ml water). The mixture was warmed to 65-70° C. for 2 hours. Progress of the reaction was monitored by TLC (methylene di-chloride (MDC): MeOH 9:1). Methanol was distilled out completely under vacuum, and the residue was dissolved in water (2000 ml). The reaction mass was cooled to 20° to 30° C., and extracted with MDC (4×100 ml.). The combined organic layer was washed with DM water (1×1000 ml). The organic layer was concentrated at 40° to 45° C., leaving 200 ml of MDC with the product. To the residue was added methanol (400 ml) at 40° to 45° C., and the mixture of MDC and methanol (400 ml) was distilled out under vacuum (50 to 100 mm Hg) at 40° to 45° C. To the residue was charged methanol (400 ml) at 40° to 45° C., and the mixture of MDC and methanol (200 ml) was distilled out under vacuum (50 to 100 mm Hg) at 40° to 45° C. To the residue were charged methanol (200 ml) and para-toluene sulfonic acid (129.8 g) at 25° to 30° C., the resultant mixture was heated to 65° to 70° C., and maintained with stirring for 60 minutes. The reaction mass was slowly cooled to 25° to 30° C. in 1 hour, and maintained for 2 hours. The crystallized solid was filtered, and the wet cake was washed with Methanol (120 ml). The product was dried under vacuum at 45° to 55° C. for 10 to 12 hours. (Yield 171.9 gm (65.81% relative to VRN-11)), HPLC purity 99.99%).

Example 12

About 200 mg of Varenicline Tosylate (Form II) was ground with a drop of water for 1 minute with a mortar and pestle. The resulting solid was analyzed by XRD, and shown to be a new Form (Form IV).

Example 13

About 200 mg of Varenicline Tosylate (Form II) was exposed to a range of 80 percent to 100 percent relative humidity (RH) for 7 days at room temperature. The resulting solid was analyzed by XRD, and shown to be a new Form (Form IV).

Example 14

About 200 mg of Varenicline Tosylate Form II entered to humidity cell of 100% relative humidity for 1 day. The resulted material was measured by XRD. According to XRD pattern Form IV was obtained.

Preparation of Varenicline-Base from Varenicline-Tosylate

Example 15

A mixture of DM water (300 ml) and 5,8,14-Triazatetracyclo[10.3.1.0$^{2,11}$.0$^{4,9}$]hexadeca-2(11),3,5,7,9-pentaene Tosylate (100 g, having a total purity of 98.74 percent, obtained in example 3) was charged into a reactor at 25-30° C., and stirred for 15 minutes. The pH was adjusted with aqueous ammonia (25 percent solution; 78 ml) to 9.5-10, and the contents were stirred at 25-30° C. for 2 hours. The material was extracted using dichloromethane (4×300 ml). The combined organic layers were washed with 300 ml of water.

Dichloromethane was distilled under vacuum to obtain 5,8,14-Triazatetracyclo[10.3.1.0$^{2,11}$.0$^{4,9}$]hexadeca-2(11),3,5,7,9-pentaene that has an HPLC purity-of 98.01 percent. Yield: 0.45-0.50 w/w (89.35% (relative to VRN-Tosylate))

Example 16

In a 250 ml 4 neck round bottom flask equipped with mechanical stirrer, Thermo pocket were charged DM water (30 ml) and 5,8,14-Triazatetracyclo[10.3.1.02,11.04,9]hexadeca-2(11),3,5,7,9-pentaene Tosylate salt (10 g, having a total purity of 99.42% obtained in example 4). The above suspension was stirred for 30 minutes at 25-30° C. To this was added 25% aqueous ammonia solution (5 ml) to adjust the pH to 9.0-10 at 25-30° C., and MDC (30 ml) was added to this solution. The resulting mixture was stirred for 30 minutes at 20-25° C. The organic layer was separated, and the aqueous layer was extracted with MDC (4×30 ml). The combined organic layer was washed with DM water (30 ml). The organic layer was treated with activated carbon (1.0 g), and stirred for 30 minutes at 25-30° C. The resulting solution filtered through celite. Concentration afforded a solid product, i.e. 5,8,14-Triazatetracyclo[10.3.1.0²,¹¹.0⁴,⁹]hexadeca-2(11),3,5,7,9-pentaene. (Yield-5 g (95.06% (relative to VRN-Tosylate)), HPLC purity-99.43%).

Example 17

A 250 ml 4 neck round bottom flask equipped with mechanical stirrer, Thermo pocket was charged with DM water (15 ml) and 5,8,14-Triazatetracyclo[10.3.1.02,11.04,9] hexadeca-2(11),3,5,7,9-pentaene Tosylate salt (5 g, having a total purity of 99.71%). The above suspension was stirred for 30 min at 25-30° C. To this was added 8% aqueous sodium bicarbonate solution (150 ml) to adjust the pH to 8.0-9.0 at 25-30° C. MDC (30 ml) was added to this solution. The resulting mixture was stirred for 30 minutes at 20-25° C. The organic layer was separated, and the aqueous layer was extracted with MDC (4×30 ml). The combined organic layer was washed with DM water (30 ml). The organic layer was treated with activated Carbon (1.0 g), and stirred for 30 minutes at 25-30° C. The resulting solution was filtered through celite. Concentration afforded a solid product i.e. 5,8,14-Triazatetracyclo[10.3.1.02,11.04,9]hexadeca-2(11),3,5,7,9-pentaene. (Yield—2.5 g (95.06% (relative to VRN-Tosylate)), HPLC purity—99.65%).

Example 18

In a 3.0 lit 4 neck round bottom flask equipped with mechanical stirrer, Thermo pocket were charged DM water (507 ml) and 5,8,14-Triazatetracyclo[10.3.1.0²,¹¹.0⁴,⁹]hexadeca-2(11),3,5,7,9-pentaene tosylate salt (169 g having a total purity of 99.99% obtained in example 6). The above suspension was stirred for 30 minutes at 25-30° C. To this was added 25% aqueous ammonia solution (60 ml) to adjust the pH to 9.0-10 at 25-30° C., and maintained with stirring for 30 minutes. MDC (507 ml) was charged in this solution. The resulting mixture was stirred for 30 minutes at 20-25° C. The layers were separated, and the aqueous layer was extracted with MDC (4×507 ml). The combined organic layer washed with DM water (507 ml). The organic layer was treated with activated Carbon (16.9 g), and stirred for 30 minutes at 25-30° C. The resulting solution was filtered through celite, concentrated to leave 1 volume of MDC with product, charged with 845 ml n-heptane at 45-50° C., and distilled under vacuum to remove a mixture of MDC and n-heptane to leave 3 volumes of n-heptane. The solid material was cooled to 25-30° C., and filtered at 25-30° C. to afford a solid product, i.e. 5,8,14-Triazatetracyclo[10.3.1.0²,¹¹.0⁴,⁹]hexadeca-2(11),3,5,7,9-pentaene. The solid obtained was dried in vacuum oven at 45° to 50° C. (Yield—84 g (94.49% (relative to VRN-Tosylate)), HPLC purity—99.97%).

Example 19

A clean and dry round bottom flask was charged with DM water (300 ml) and 5,8,14-Triazatetracyclo[10.3.1.0²,¹¹.04, 9]hexadeca-2(11),3,5,7,9-pentaene tosylate salt (10 g, having a total purity of 99.94%) at 20-30° C. The pH of the mixture was adjusted to 12.5-13.5 using 30% aqueous sodium hydroxide solution (50 ml) at 20-30° C., and maintained for 30 minutes. To the clear solution obtained was charged toluene (500 ml) at 20-30° C., and the temperature was raised to 50-60° C., and maintained for 30 minutes. The aqueous layer was separated, and the pH was adjusted to 12.5-13.5, and the layer was extracted with toluene (4×500 ml) at 50-60° C. To the combined organic layers were charged activated carbon (10 g) and neutral aluminum oxide (10 g) at 50-60° C. The resulting mixture was stirred for 60 minutes at 50-60° C., filtered through a celite bed (20 g) at 50-60° C., and the celite bed was washed with toluene (200 ml). The filtrate was distilled out under vacuum (50-100 mm Hg) at 50-60° C. leaving 200 ml toluene with compound. To the residue was charged n-heptane (200 ml) at 50-60° C., and a mixture of n-heptane and toluene (200 ml) was distilled out under vacuum (50-100 mm Hg) at 50-60° C. Again, n-heptane (200 ml) was charged to the residue at 50-60° C., and a mixture of n-heptane and toluene (200 ml) was distilled out under vacuum (50-100 mm Hg) at 50-60° C. To the resultant slurry was charged n-heptane (100 ml) at 50-60° C., and the resulting mixture was cooled to 20-30° C. and maintained for 1 hour. The precipitated solid was filtered and washed with n-heptane (100 ml) at 20-30° C. The wet cake was dried under vacuum (20-50 mm Hg) at 50-60° C. for 10-12 hours.

Yield: 0.45-0.50 w/w (91.25% (relative to VRN-Tosylate)). HPLC purity 99.97%.

What is claimed is:

1. A crystalline form of Varenicline Tosylate, designated form II, characterized by data selected from the group consisting of:
   a powder X-ray diffraction pattern having peaks at 11.6, 12.9, 13.3, 20.8, and 21.3±0.2 degrees two theta;
   a powder X-ray diffraction pattern having peaks at 11.6, 12.9, 13.3, 21.3, and 23.3±0.2 degrees two theta;
   a powder X-ray diffraction pattern having peaks at 5.8, 10.0, 17.4, 19.1, and 23.3±0.1 degrees two theta;
   and
   combinations thereof.

2. The crystalline form of claim 1, characterized by a powder X-ray diffraction pattern having peaks at 11.6, 12.9, 13.3, 21.3, and 23.3±0.2 degrees two theta.

3. The crystalline form of claim 1, characterized by a powder X-ray diffraction pattern having peaks at 5.8, 10.0, 17.4, 19.1, and 23.3±0.1 degrees two theta.

4. The crystalline form of claim 1, further characterized by powder X-ray diffraction pattern peaks selected from a group consisting of:
   a powder X-ray diffraction pattern having peaks at 5.8, 10.0, 16.9, 17.4, and 18.8±0.2 degrees two theta;
   a powder X-ray diffraction pattern having peaks at 11.5, 13.2, 20.8, 22.5 and 25.4±0.1 degrees two theta; and
   combinations thereof.

5. A process for preparing the Varenicline tosylate crystalline form of claim 1, comprising: heating a mixture of Varenicline base in methanol, $C_6$-$C_{12}$ aromatic hydrocarbon, and p-toluene sulfonic acid, and cooling the mixture.

6. A process for preparing the Varenicline Tosylate crystalline form of claim 1, comprising: combining Varenicline base, methanol, a $C_6$-$C_{12}$ aromatic hydrocarbon, and p-toluene sulfonic acid to obtain a reaction mixture, and heating and then cooling the obtained reaction mixture.

7. The process of claim 6, wherein the $C_6$-$C_{12}$ aromatic hydrocarbon is toluene or xylene.

8. The process of claim 6, wherein the $C_6$-$C_{12}$ aromatic hydrocarbon is toluene.

9. The process of claim 6, wherein Varenicline base and p-toluene sulfonic acid are combined in a mixture of about 15 percent to about 30 percent volume $C_6$-$C_{12}$ aromatic hydrocarbon and about 70 percent to about 85 percent volume methanol.

10. The process of claim 6, wherein the reaction mixture is heated to a temperature of from about 65° C. to about 70° C.

11. The process of claim 6, wherein the reaction mixture is cooled to a temperature of from about 30° C. to about 20° C.

* * * * *